(12) United States Patent
Kim et al.

(10) Patent No.: US 7,319,900 B2
(45) Date of Patent: Jan. 15, 2008

(54) CARDIAC RESPONSE CLASSIFICATION USING MULTIPLE CLASSIFICATION WINDOWS

(75) Inventors: Jaeho Kim, Redmond, WA (US); Joseph Bocek, Seattle, WA (US); Scott A. Meyer, Rochester, MN (US); Paul A. Haefner, Circle Pines, MN (US); Haris J. Sih, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 292 days.

(21) Appl. No.: 10/733,869

(22) Filed: Dec. 11, 2003

(65) Prior Publication Data

US 2005/0131476 A1 Jun. 16, 2005

(51) Int. Cl.
*A61N 1/37* (2006.01)
(52) U.S. Cl. .......................... 607/27; 607/28
(58) Field of Classification Search .............. 607/9, 607/26–28; 600/510
See application file for complete search history.

(56) References Cited

U.S. PATENT DOCUMENTS

| | | | |
|---|---|---|---|
| 3,920,005 A | 11/1975 | Gombrich et al. | |
| 5,222,493 A | 6/1993 | Sholder | |
| 5,271,411 A | 12/1993 | Ripley et al. | |
| 5,350,410 A * | 9/1994 | Kleks et al. | 607/28 |
| 5,431,693 A * | 7/1995 | Schroeppel | 607/28 |
| 5,443,485 A * | 8/1995 | Housworth et al. | 607/28 |
| 5,626,620 A | 5/1997 | Kieval et al. | |
| 5,683,431 A | 11/1997 | Wang | |
| 5,683,434 A * | 11/1997 | Archer | 607/36 |
| 6,101,416 A * | 8/2000 | Sloman | 607/28 |
| 6,128,535 A | 10/2000 | Maarse | |
| 6,163,724 A | 12/2000 | Hemming et al. | |
| 6,169,921 B1 | 1/2001 | KenKnight et al. | |
| 6,175,766 B1 | 1/2001 | Bornzin et al. | |
| 6,192,275 B1 * | 2/2001 | Zhu et al. | 607/28 |
| 6,275,731 B1 * | 8/2001 | Zhu et al. | 607/9 |
| 6,324,427 B1 * | 11/2001 | Florio | 607/28 |
| 6,449,503 B1 | 9/2002 | Hsu | |
| 6,505,071 B1 * | 1/2003 | Zhu et al. | 607/28 |
| 6,512,953 B2 * | 1/2003 | Florio et al. | 607/28 |
| 6,567,701 B2 * | 5/2003 | Vonk | 607/28 |
| 6,615,082 B1 * | 9/2003 | Mandell | 607/11 |
| 6,950,702 B2 * | 9/2005 | Sweeney | 607/26 |
| 6,973,350 B1 * | 12/2005 | Levine et al. | 607/27 |
| 7,027,868 B2 * | 4/2006 | Rueter et al. | 607/28 |
| 2002/0095188 A1 | 7/2002 | Mower | |
| 2002/0183798 A1 * | 12/2002 | Vonk | 607/28 |
| 2003/0050671 A1 * | 3/2003 | Bradley | 607/27 |
| 2003/0083710 A1 | 5/2003 | Ternes et al. | |
| 2003/0083711 A1 * | 5/2003 | Yonce et al. | 607/27 |
| 2004/0171959 A1 * | 9/2004 | Stadler et al. | 600/518 |

* cited by examiner

FOREIGN PATENT DOCUMENTS

EP 0 468 720 A 1/1992

*Primary Examiner*—George R. Evanisko
(74) *Attorney, Agent, or Firm*—Hollingsworth & Funk, LLC

(57) ABSTRACT

Methods and devices for classifying a cardiac response to pacing involve establishing a plurality of classification windows relative to and following a pacing pulse. One or more characteristics of a cardiac signal sensed following the pacing pulse are detected within one or more particular classification windows. The characteristics may be compared to one or more references. Classification of the cardiac response may be performed based on the comparison of the one or more characteristics to the one or more references and the particular classification windows in which the one or more characteristics are detected.

88 Claims, 28 Drawing Sheets

Slope is flat

CARDIAC RESPONSE CLASSIFICATION USING MULTIPLE CLASSIFICATION WINDOWS

FIELD OF THE INVENTION

The present invention relates generally to implantable medical devices and, more particularly, to classifying a cardiac response following delivery of a pace pulse.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal following the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

At times, a pacing pulse may merge with an intrinsic beat, producing a fusion beat. A fusion beat is a cardiac contraction that occurs when two cardiac depolarizations of a particular chamber, but from separate initiation sites, merge. When the heart is being paced, a fusion beat may occur when an intrinsic cardiac depolarization of a particular chamber merges with a pacer output pulse within that chamber. Fusion beats, as seen on electrocardiographic recordings, exhibit various morphologies. The merging depolarizations of a fusion beat do not contribute evenly to the total depolarization.

Pseudofusion occurs when a pacer output pulse is superimposed upon a spontaneous P wave during atrial pacing or upon a spontaneous QRS complex during ventricular pacing. In pseudofusion, the pacing stimulus may be ineffective because the tissue around the electrode has already spontaneously depolarized and is in its refractory period.

During normal pacing, the presence of fusion or pseudofusion beats may be of little consequence except for wasted energy due to the generation of unnecessary pace pulses. However, detection of fusion of pseudofusion beats may be required during an automatic capture or threshold determination procedures. Fusion or pseudofusion beats may cause false detection of capture and may lead to erroneous capture threshold values.

Capture may be verified by detecting if a cardiac signal following a pace pulse indicates a captured response. However, the captured response must be discerned from other responses, including the superimposed residual post pace polarization without capture, intrinsic beats, and fusion/pseudofusion beats.

SUMMARY OF THE INVENTION

The present invention involves various methods and devices for classifying cardiac responses to pacing stimulation. In accordance with one embodiment of the invention, a method of classifying a cardiac response to a pacing stimulation involves defining a plurality of classification windows relative and subsequent to a pacing stimulation. A cardiac signal following the pacing stimulation is sensed and a characteristic of the cardiac signal is detected within a particular classification window of the plurality of classification windows. The cardiac response is classified based on the detected characteristic and the particular classification window.

Another embodiment of the invention involves a method for determining cardiac responses to pacing pulses. The method involves delivering a sequence of pacing pulses to the heart. A plurality of classification windows are defined relative to and subsequent to each of the pacing pulses. Cardiac signals are sensed following the pacing pulses. One or more characteristics of the cardiac signals are detected within particular classification windows. The detected cardiac signal characteristics s are compared to one or more references respectively associated with types of cardiac pacing responses. The cardiac pacing responses are classified based on the comparisons and the particular classification windows in which the characteristics are detected.

Yet another embodiment of the invention involves a method for classifying a cardiac pacing response. The method involves delivering a pacing stimulation to the heart and defining a plurality of classification windows relative and subsequent to the pacing stimulation. A cardiac signal responsive to the pacing stimulation is sensed and the peak of the sensed cardiac signal is detected within a particular classification window. The cardiac response is determined based on the detected peak and the particular classification window.

In accordance with yet another embodiment of the invention, a medical device for classifying a cardiac response to pacing includes a pacing pulse delivery circuit configured to deliver a pacing pulse to a heart. The medical device further includes a sensing circuit configured to sense a cardiac signal associated with the pacing pulse. A control circuit is coupled to the sensing circuit. The control circuit is configured to define a plurality of classification windows relative to and following the pacing pulse, detect a characteristic of the cardiac signal sensed within a particular classification window, and classify a cardiac response to the pacing pulse based on the detected characteristic and the particular classification window.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
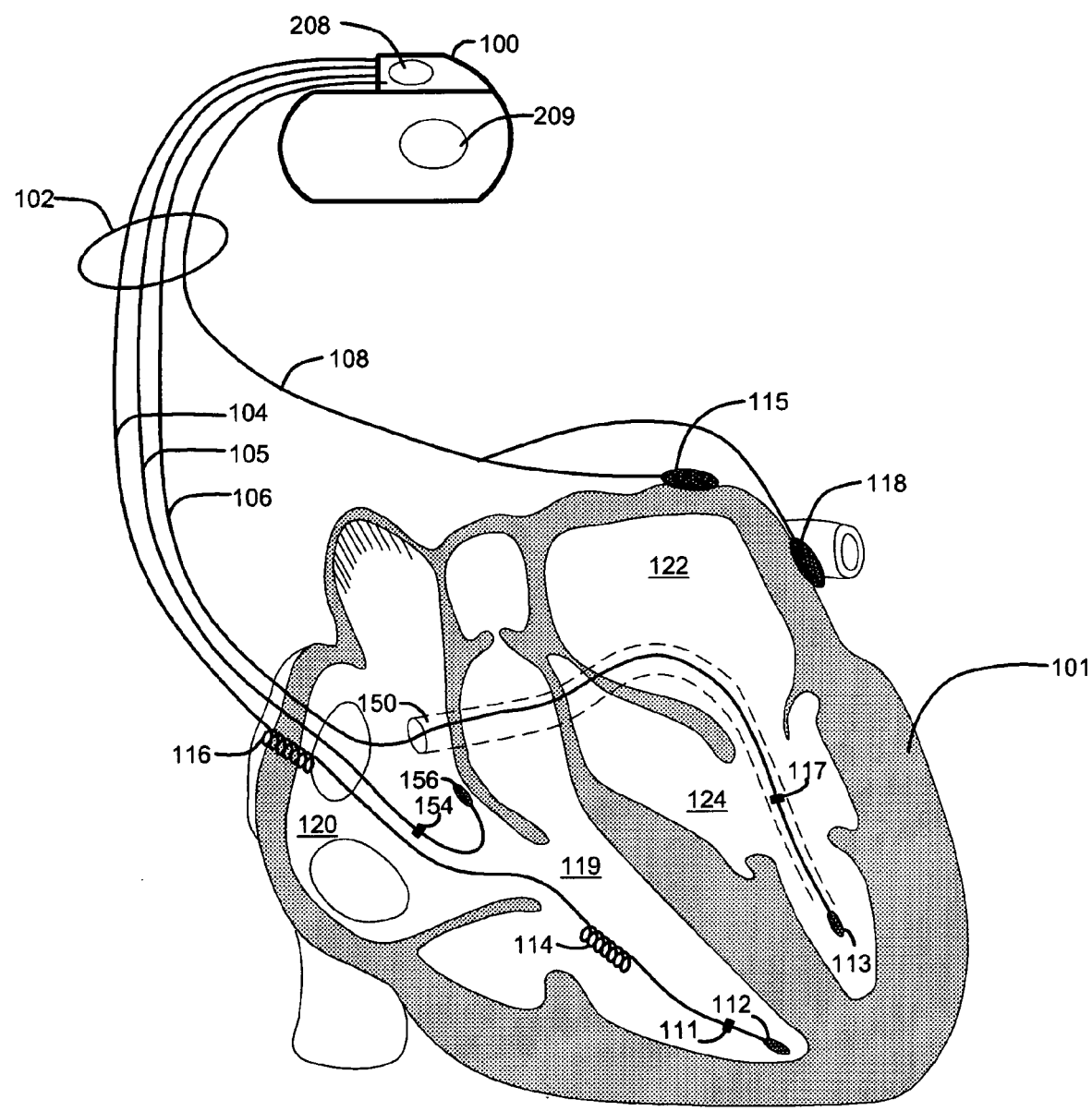
FIG. 1 is a partial view of one embodiment of an implantable medical device in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Embodiments of the invention are directed methods and devices for classifying the cardiac response following the delivery of pacing stimulation to the heart. In accordance with various aspects of the invention, cardiac response classification may be implemented by defining a plurality of classification windows relative to and following a pacing stimulation.

The pacing stimulation may be delivered to any heart chamber. For example, the pacing stimulation may be delivered to one of the right ventricle, the left ventricle, the right atrium, and the left atrium.

A cardiac signal following the pacing stimulation is sensed. One or more characteristics of the cardiac signal, for example, a peak, slope, curvature, sequence of feature points, or other characteristic of the cardiac signal are detected in one or more particular classification windows. The cardiac response to the pacing stimulation is determined based on the one or more detected characteristics and the one or more particular classification windows in which the one or more characteristics are detected. The cardiac response may be determined to be one of a captured response, a non-captured response, a non-captured response added to an intrinsic beat, a fusion/pseudofusion beat, and noise, for example.

Various embodiments of the invention involve using the same electrode combination for pacing and sensing. Other embodiments involve using an electrode combination for pacing that is different from the electrode combination used for sensing the cardiac response to pacing. Employing different electrode combinations for pacing and sensing may enhance cardiac response classification. For example, using different electrode combinations for pacing and sensing may facilitate detection of fusion/pseudofusion beats. Further, such a configuration may be used to enhance discrimination of fusion/pseudofusion beats from captured beats.

By way of example, the processes of the present invention may be used to enhance capture threshold testing to determine the optimal energy for pacing. Determination of the optimal pacing energy may be implemented, for example, by an automatic capture threshold testing procedure executed by an implantable cardiac rhythm management system. Additionally, automatic capture verification may be used to monitor pacing on a beat-by-beat basis. Automatic capture verification may be used to control back up pacing when a pace pulse delivered to the heart fails to evoke a captured response (CR). These and other applications may be enhanced by employment of the systems and methods of the present invention.

Those skilled in the art will appreciate that reference to a capture threshold procedure indicates a method of determining the capture threshold in one of left atrium, right atrium, left ventricle, and right ventricle. In such a procedure, the pacemaker, automatically or upon command, initiates a search for the capture threshold of the selected heart chamber. The capture threshold is defined as the lowest pacing energy that consistently captures the heart.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture events occur. The pacemaker may increase the stimulation energy in discrete steps until a predetermined number of capture events occur to confirm the capture threshold. A capture threshold test may be performed using cardiac response classification methods of the present invention.

Other procedures for implementing capture threshold testing may be utilized. In one example, the pacing energy may be increased in discrete steps until capture is detected. In another example, the pacing energy may be adjusted according to a binomial search pattern.

Automatic capture threshold determination is distinguishable from automatic capture detection, a procedure that may occur on a beat-by-beat basis during pacing. Automatic capture detection verifies that a delivered pace pulse results in a captured response. When a captured response is not detected following a pace pulse, the pacemaker may deliver a back up safety pace to ensure consistent pacing. The back up pace may be delivered, for example, about 70-80 ms after the initial pace pulse. If a predetermined number of pace pulses delivered during normal pacing do not produce a captured response, the pacemaker may initiate a capture threshold test to determine the capture threshold. Automatic capture detection and back up pacing may be implemented using the cardiac response classification processes of the present invention.

The embodiments of the present system illustrated herein are generally described as being implemented in an implantable cardiac defibrillator (ICD) that may operate in numerous pacing modes known in the art. Various types of single and multiple chamber implantable cardiac defibrillators are known in the art and may be used in connection with the cardiac response classification methods of the present invention. The methods of the present invention may also be implemented in a variety of implantable or patient-external cardiac rhythm management devices, including single and multi chamber pacemakers, defibrillators, cardioverters, bi-ventricular pacemakers, cardiac resynchronizers, and cardiac monitoring systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Referring now to FIG. 1 of the drawings, there is shown a cardiac rhythm management system that may be used to implement cardiac response classification methods of the present invention. The cardiac rhythm management system in FIG. 1 includes an ICD 100 electrically and physically coupled to a lead system 102. The housing and/or header of the ICD 100 may incorporate one or more electrodes 208, 209 used to provide electrical stimulation energy to the heart and to sense cardiac electrical activity. The ICD 100 may utilize all or a portion of the ICD housing as a can electrode 209. The ICD 100 may include an indifferent electrode positioned, for example, on the header or the housing of the ICD 100. If the ICD 100 includes both a can electrode 209 and an indifferent electrode 208, the electrodes 208, 209 typically are electrically isolated from each other.

The lead system 102 is used to detect electric cardiac signals produced by the heart 101 and to provide electrical energy to the heart 101 under certain predetermined conditions to treat cardiac arrhythmias. The lead system 102 may include one or more electrodes used for pacing, sensing, and/or defibrillation. In the embodiment shown in FIG. 1, the lead system 102 includes an intracardiac right ventricular (RV) lead system 104, an intracardiac right atrial (RA) lead system 105, an intracardiac left ventricular (LV) lead system 106, and an extracardiac left atrial (LA) lead system 108. The lead system 102 of FIG. 1 illustrates one embodiment that may be used in connection with the cardiac response classification methodologies described herein. Other leads and/or electrodes may additionally or alternatively be used.

The lead system 102 may include intracardiac leads 104, 105, 106 implanted in a human body with portions of the intracardiac leads 104, 105, 106 inserted into a heart 101. The intracardiac leads 104, 105, 106 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 1, the lead system 102 may include one or more extracardiac leads 108 having electrodes, e.g., epicardial electrodes, positioned at locations outside the heart for sensing and pacing one or more heart chambers.

The right ventricular lead system 104 illustrated in FIG. 1 includes an SVC-coil 116, an RV-coil 114, an RV-ring electrode 111, and an RV-tip electrode 112. The right ventricular lead system 104 extends through the right atrium 120 and into the right ventricle 119. In particular, the RV-tip electrode 112, RV-ring electrode 111, and RV-coil electrode 114 are positioned at appropriate locations within the right ventricle 119 for sensing and delivering electrical stimulation pulses to the heart. The SVC-coil 116 is positioned at an appropriate location within the right atrium chamber 120 of the heart 101 or a major vein leading to the right atrial chamber 120 of the heart 101.

In one configuration, the RV-tip electrode 112 referenced to the can electrode 209 may be used to implement unipolar pacing and/or sensing in the right ventricle 119. Bipolar pacing and/or sensing in the right ventricle may be implemented using the RV-tip 112 and RV-ring 111 electrodes. In yet another configuration, the RV-ring 111 electrode may optionally be omitted, and bipolar pacing and/or sensing may be accomplished using the RV-tip electrode 112 and the RV-coil 114, for example. The right ventricular lead system 104 may be configured as an integrated bipolar pace/shock lead. The RV-coil 114 and the SVC-coil 116 are defibrillation electrodes.

The left ventricular lead 106 includes an LV distal electrode 113 and an LV proximal electrode 117 located at appropriate locations in or about the left ventricle 124 for pacing and/or sensing the left ventricle 124. The left ventricular lead 106 may be guided into the right atrium 120 of the heart via the superior vena cava. From the right atrium 120, the left ventricular lead 106 may be deployed into the coronary sinus ostium, the opening of the coronary sinus 150. The lead 106 may be guided through the coronary sinus 150 to a coronary vein of the left ventricle 124. This vein is used as an access pathway for leads to reach the surfaces of the left ventricle 124 which are not directly accessible from the right side of the heart. Lead placement for the left ventricular lead 106 may be achieved via subclavian vein access and a preformed guiding catheter for insertion of the LV electrodes 113, 117 adjacent to the left ventricle.

Unipolar pacing and/or sensing in the left ventricle may be implemented, for example, using the LV distal electrode referenced to the can electrode 209. The LV distal electrode 113 and the LV proximal electrode 117 may be used together as bipolar sense and/or pace electrodes for the left ventricle. The left ventricular lead 106 and the right ventricular lead 104, in conjunction with the ICD 100, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 105 includes a RA-tip electrode 156 and an RA-ring electrode 154 positioned at appropriate locations in the right atrium 120 for sensing and pacing the right atrium 120. In one configuration, the RA-tip 156 referenced to the can electrode 209, for example, may be used to provide unipolar pacing and/or sensing in the right atrium 120. In another configuration, the RA-tip electrode 156 and the RA-ring electrode 154 may be used to effect bipolar pacing and/or sensing.

FIG. 1 illustrates one embodiment of a left atrial lead system 108. In this example, the left atrial lead 108 is implemented as an extracardiac lead with LA distal 118 and LA proximal 115 electrodes positioned at appropriate locations outside the heart 101 for sensing and pacing the left atrium 122. Unipolar pacing and/or sensing of the left atrium may be accomplished, for example, using the LA distal electrode 118 to the can 209 pacing vector. The LA proximal 115 and LA distal 118 electrodes may be used together to implement bipolar pacing and/or sensing of the left atrium 122.

Figure 2A:
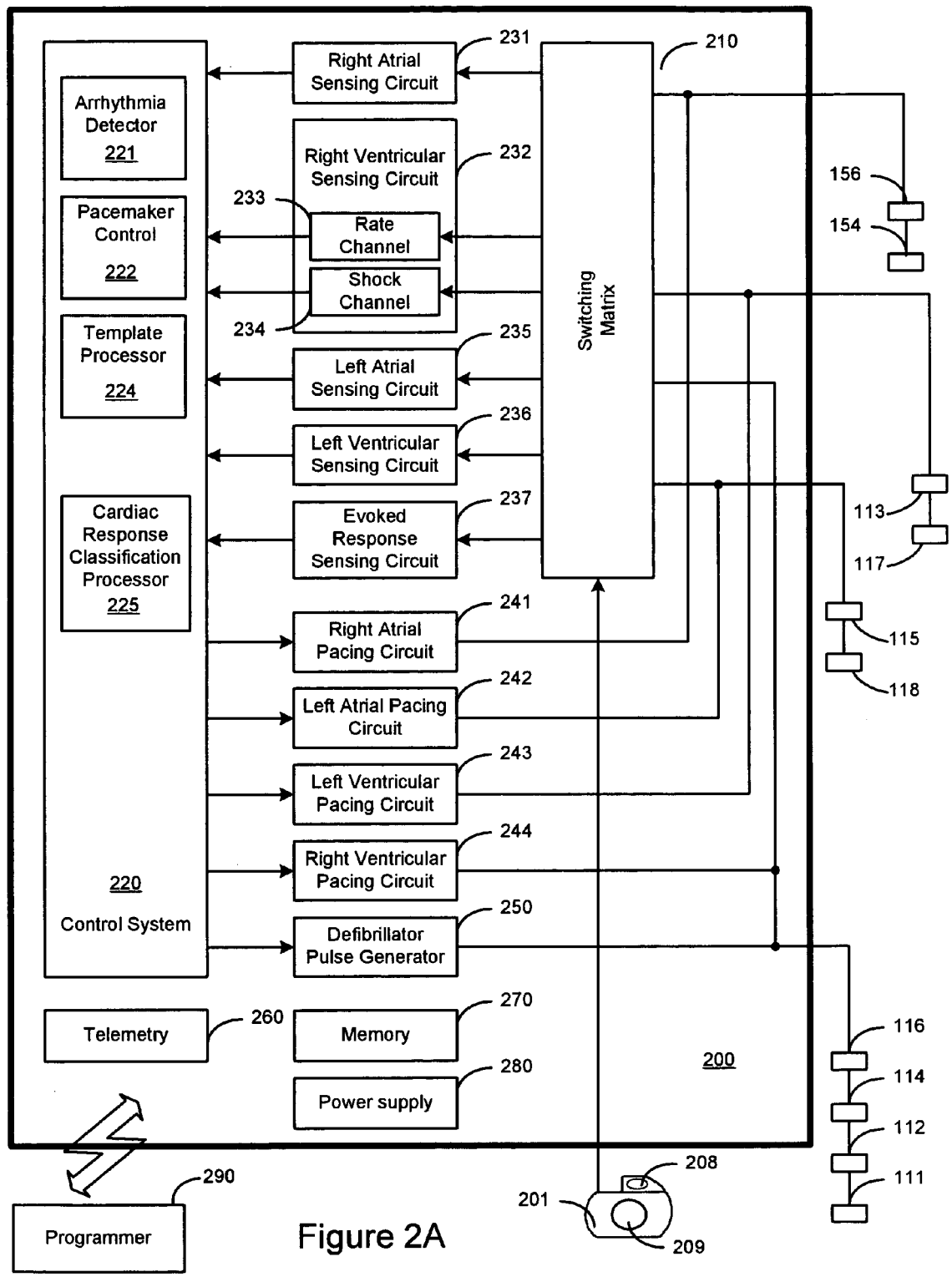
FIG. 2A is a block diagram of an implantable medical device that may be used to classify a cardiac response to pacing in accordance with embodiments of the invention.

Referring now to FIG. 2A, there is shown an embodiment of a cardiac defibrillator 200 suitable for implementing a cardiac response classification methodology of the present invention. FIG. 2A shows a cardiac defibrillator divided into functional blocks. It is understood by those skilled in the art that there exist many possible configurations in which these functional blocks can be arranged. The example depicted in FIG. 2A is one possible functional arrangement. Other arrangements are also possible. For example, more, fewer or different functional blocks may be used to describe a cardiac defibrillator suitable for implementing the cardiac response classification methodology of the present invention. In addition, although the cardiac defibrillator 200 depicted in FIG. 2A contemplates the use of a programmable microprocessor-based logic circuit, other circuit implementations may be utilized.

The cardiac defibrillator 200 depicted in FIG. 2A includes circuitry for receiving cardiac signals from a heart and delivering electrical stimulation energy to the heart in the form of pacing pulses or defibrillation shocks. In one embodiment, the circuitry of the cardiac defibrillator 200 is encased and hermetically sealed in a housing 201 suitable for implanting in a human body. Power to the cardiac defibrillator 200 is supplied by an electrochemical battery 280. A connector block (not shown) is attached to the housing 201 of the cardiac defibrillator 200 to allow for the physical and electrical attachment of the lead system conductors to the circuitry of the cardiac defibrillator 200.

The cardiac defibrillator 200 may be a programmable microprocessor-based system, including a control system 220 and a memory 270. The memory 270 may store parameters for various pacing, defibrillation, and sensing modes, along with other parameters. Further, the memory 270 may store data indicative of cardiac signals received by other components of the cardiac defibrillator 200. The memory 270 may be used, for example, for storing historical EGM and therapy data. The historical data storage may include, for example, data obtained from long term patient monitoring used for trending or other diagnostic purposes. Historical data, as well as other information, may be transmitted to an external programmer unit 290 as needed or desired.

The control system 220 and memory 270 may cooperate with other components of the cardiac defibrillator 200 to control the operations of the cardiac defibrillator 200. The control system depicted in FIG. 2A incorporates a cardiac response classification processor 225 for classifying cardiac responses to pacing stimulation in accordance with various embodiments of the present invention. The control system 220 may include additional functional components including a pacemaker control circuit 222, an arrhythmia detector 221, and a template processor 224, along with other components for controlling the operations of the cardiac defibrillator 200.

Telemetry circuitry 260 may be implemented to provide communications between the cardiac defibrillator 200 and an external programmer unit 290. In one embodiment, the telemetry circuitry 260 and the programmer unit 290 communicate using a wire loop antenna and a radio frequency telemetric link, as is known in the art, to receive and transmit signals and data between the programmer unit 290 and the telemetry circuitry 260. In this manner, programming commands and other information may be transferred to the control system 220 of the cardiac defibrillator 200 from the programmer unit 290 during and after implant. In addition, stored cardiac data pertaining to capture threshold, capture detection and/or cardiac response classification, for example, along with other data, may be transferred to the programmer unit 290 from the cardiac defibrillator 200.

In the embodiment of the cardiac defibrillator 200 illustrated in FIG. 2A, electrodes RA-tip 156, RA-ring 154, RV-tip 112, RV-ring 111, RV-coil, SVC-coil, LV distal electrode 113, LV proximal electrode 117, LA distal electrode 118, LA proximal electrode 115, indifferent electrode 208, and can electrode 209 are coupled through a switch matrix 210 to sensing circuits 231-237.

A right atrial sensing circuit 231 serves to detect and amplify electrical signals from the right atrium of the heart. Bipolar sensing in the right atrium may be implemented, for example, by sensing voltages developed between the RA-tip 156 and the RA-ring 154. Unipolar sensing may be implemented, for example, by sensing voltages developed between the RA-tip 156 and the can electrode 209. Outputs from the right atrial sensing circuit are coupled to the control system 220.

A right ventricular sensing circuit 232 serves to detect and amplify electrical signals from the right ventricle of the heart. The right ventricular sensing circuit 232 may include, for example, a right ventricular rate channel 233 and a right ventricular shock channel 234. Right ventricular cardiac signals sensed through use of the RV-tip 112 electrode are right ventricular near-field signals and are denoted RV rate channel signals. A bipolar RV rate channel signal may be sensed as a voltage developed between the RV-tip 112 and the RV-ring. Alternatively, bipolar sensing in the right ventricle may be implemented using the RV-tip electrode 112 and the RV-coil 114. Unipolar rate channel sensing in the right ventricle may be implemented, for example, by sensing voltages developed between the RV-tip 112 and the can electrode 209.

Right ventricular cardiac signals sensed through use of the RV-coil electrode 114 are far-field signals, also referred to as RV morphology or RV shock channel signals. More particularly, a right ventricular shock channel signal may be detected as a voltage developed between the RV-coil 114 and the SVC-coil 116. A right ventricular shock channel signal may also be detected as a voltage developed between the RV-coil 114 and the can electrode 209. In another configuration the can electrode 209 and the SVC-coil electrode 116 may be electrically shorted and a RV shock channel signal may be detected as the voltage developed between the RV-coil 114 and the can electrode 209/SVC-coil 116 combination.

Outputs from the right ventricular sensing circuit 232 are coupled to the control system 220. In one embodiment of the invention, rate channel signals and shock channel signals may be used to develop morphology templates for analyzing cardiac signals. In this embodiment, rate channel signals and shock channel signals may be transferred from the right ventricular sensing circuit 232 to the control system 220 and to a template processor 224 where the morphological characteristics of a cardiac signal are analyzed. The template processor 224 works in combination with the control system 220 and the memory 270 to generate and maintain various types of templates, including, for example, templates used for arrhythmia discrimination as well as cardiac response classification as described in more detail below.

Left atrial cardiac signals may be sensed through the use of one or more left atrial electrodes 115, 118, which may be configured as epicardial electrodes. A left atrial sensing circuit 235 serves to detect and amplify electrical signals from the left atrium of the heart. Bipolar sensing and/or pacing in the left atrium may be implemented, for example, using the LA distal electrode 118 and the LA proximal electrode 115. Unipolar sensing and/or pacing of the left atrium may be accomplished, for example, using the LA distal electrode 118 to can vector 209 or the LA proximal electrode 115 to can vector 209.

A left ventricular sensing circuit 236 serves to detect and amplify electrical signals from the left ventricle of the heart. Bipolar sensing in the left ventricle may be implemented, for example, by sensing voltages developed between the LV distal electrode 113 and the LV proximal electrode 117. Unipolar sensing may be implemented, for example, by sensing voltages developed between the LV distal electrode 113 or the LV proximal electrode 117 to the can electrode 209.

Optionally, an LV coil electrode (not shown) may be inserted into the patient's cardiac vasculature, e.g., the coronary sinus, adjacent the left heart. Signals detected using combinations of the LV electrodes, 113, 117, LV coil electrode (not shown), and/or can electrodes 209 may be sensed and amplified by the left ventricular sensing circuitry 236. The output of the left ventricular sensing circuit 236 is coupled to the control system 220.

The outputs of the switching matrix 210 may be operated to couple selected combinations of electrodes 111, 112, 113, 114, 115, 116, 117, 118, 156, 154 to an evoked response sensing circuit 237. The evoked response sensing circuit 237 serves to sense and amplify voltages developed using various combinations of electrodes for cardiac response classification in accordance with embodiments of the invention.

In the embodiments described below, various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing.

Sensing the cardiac signal following a pacing pulse using the same electrode combination for both pacing and sensing may yield a sensed cardiac signal including a pacing artifact component associated with residual post pace polarization at the electrode-tissue interface. The pacing artifact component may be superimposed on a smaller signal indicative of the cardiac response to the pacing pulse, i.e., the evoked response. The pacing output circuitry may include a coupling capacitor to block DC components from the heart and to condition the pacing stimulus pulse. A relatively large coupling capacitor may cause a larger pacing artifact that decays exponentially over a relatively long period of time.

The presence of a large pacing artifact signal may complicate the classification of the cardiac response to pacing. Various embodiments of the invention are directed to methods involving detection of a cardiac signal following pacing and canceling the pacing artifact from the detected signal. Classification of the cardiac response to pacing is implemented using the pacing artifact cancelled signal. Cancellation of the pacing artifact in cardiac response classification is particularly important when the same or similar electrode combinations are used both for delivering pacing pulses and for sensing the cardiac signals following the delivery of the pacing pulses. Cancellation of the pacing artifact may also be used when a first electrode combination is used for pacing the heart chamber and a different electrode combination is used to sense the subsequent cardiac response.

In various embodiments described herein a first electrode combination may be used for pacing the heart chamber and a second electrode combination used for sensing the cardiac signals following the pace for cardiac response classification. If different electrode combinations are used for pacing and sensing, a temporal separation between the cardiac response signal, e.g., the evoked response, and the pacing artifact may facilitate classification of the cardiac response to pacing. The temporal separation occurs due to the propagation delay of the depolarization wavefront initiated at the pacing electrode and traveling to a sensing electrode that is physically spaced apart from the pacing electrode. The temporal separation of the cardiac response signal and the pacing artifact may be sufficient to obviate cancellation of the pacing artifact. Use of different electrodes for pacing and sensing in connection with capture verification is described in commonly owned U.S. Pat. No. 6,128,535 which is incorporated herein by reference.

The pacemaker control circuit 222, in combination with pacing circuitry for the left atrium, right atrium, left ventricle, and right ventricle 241, 242, 243, 244, may be implemented to selectively generate and deliver pacing pulses to the heart using various electrode combinations. The pacing electrode combinations may be used to effect bipolar or unipolar pacing of the heart chambers as described above.

As described above, bipolar or unipolar pacing pulses may be delivered to a heart chamber using one of the pacing vectors as described above. The electrical signal following the delivery of the pacing pulses may be sensed through various sensing vectors coupled through the switch matrix 210 to the evoked response sensing circuit 237 and used to classify the cardiac response to pacing.

In one example, the cardiac signal following the pacing pulse may be sensed using the same vector as was used for delivery of the pacing pulse. In this scenario, the pacing artifact may be canceled from the sensed cardiac signal using the pacing artifact cancellation techniques described below. Following cancellation of the pacing artifact, multiple cardiac response classification windows may be defined following the pacing pulse and used to classify the cardiac response to pacing. The cardiac response may be classified as one of a captured response, a non-captured response, a non-captured response and an intrinsic beat, a fusion/pseudofusion beat, and noise, for example.

In another example, the vector used to sense the cardiac signal following the pacing pulse may be different from the vector that was used to deliver the pacing pulse. The sensing vector may be selected to minimize the pacing artifact. Cancellation of the pacing artifact may not be necessary if the pacing artifact is sufficiently minimized using this technique.

In one embodiment, the cardiac signal sensed using a sensing vector different from the pacing vector may be used to detect fusion/pseudofusion beats. In another embodiment, the cardiac signal sensed using a sensing vector different from the pacing vector may be used to discriminate between fusion/pseudofusion beats and captured beats. In other embodiments, the cardiac response to the pacing stimulation may be classified as one of a captured response, a non-captured response, a non-captured response and an intrinsic beat, a fusion/pseudofusion beat, and noise, for example. In various embodiments, the pacing pulse may be delivered using electrodes associated with a near-field vector and the sensing vector may be a far-field vector. In an example of right ventricular pacing and cardiac response sensing, the pacing vector may be the rate channel vector and the sensing vector may be the shock channel vector. Cardiac response classification may be accomplished, for example, using multiple classification windows defined following delivery of the pacing pulse as described in greater detail below.

Possible sensing vectors for effecting cardiac response classification may include, for example, RV-tip 112 and RV-coil 114, RV-coil 114 and LV distal electrode 113, RV coil 114 and LV proximal electrode 117, RV-coil 114 and can 209, RV-coil 114 and SVC coil 116, RV-coil 114 and SVC coil 116 tied and the can 209, RV-coil 114 and A-ring 154, RV-coil 114 and RA-tip 156, LV distal electrode 113 and LV proximal electrode 117, LV distal electrode 113 and can 209, LV distal electrode 113 and SVC coil 116, LV distal electrode 113 and A-ring 154, LV distal electrode 113 and A-tip 156, LV proximal electrode 117 and can 209, LV proximal electrode 117 and SVC coil 116, LV proximal electrode 117 and A-ring 154, LV proximal electrode 117 and RA-tip 156, SVC coil 116 and can 209, RA-ring 154 and can 209, RA-tip 156 and can 209, SVC coil 116 and A-ring 154, SVC coil 116 and RA-tip 156 and RA-ring 154 and RA-tip 156. This list is not exhaustive and other sensing vector combinations may be developed to implement cardiac response classification in accordance with embodiments of the invention. For example, other combinations may include a coronary sinus electrode, an indifferent electrode, a leadless ECG electrode, cardiac epicardial electrodes, subcutaneous electrodes, and/or other electrodes.

Approaches for using leadless ECG electrodes for capture detection are described in U.S. Pat. No. 5,222,493, which is incorporated by reference in its entirety.

Subcutaneous electrodes may provide additional sensing vectors useable for cardiac response classification. In one implementation, cardiac rhythm management system may involve a hybrid system including a first device, e.g. a pacemaker coupled to an intracardiac lead system, configured to pace the heart, and a second device, e.g. a defibrillator coupled to a subcutaneous lead system, configured to perform functions other than pacing. The second device may be employed to detect and classify cardiac responses to pacing based on signals sensed using subcutaneous electrode arrays. The first and second devices may operate cooperatively with communication between the devices occurring over a wireless link, for example. Examples of subcutaneous electrode systems and devices are described in commonly owned U.S. patent application Ser. No. 10/462,001, filed Jun. 13, 2003 and Ser. No. 10/465,520, filed Jun. 19, 2003, which are incorporated herein by reference in their respective entireties.

For right ventricular pacing, bipolar pacing may be delivered using the RV-tip electrode 112 and the RV-ring electrode 111. Unipolar pacing may be delivered using the RV-tip 112 to can 209 vector. The preferred sensing electrode combinations for cardiac response classification following RV pacing include RV-coil 114 to SVC-coil 116 tied to the can electrode 209, RV-coil 114 to can electrode 209, and, if the system includes an left ventricular lead, LV distal electrode 113 to LV proximal electrode 117.

In an example of left ventricular pacing, bipolar pacing pulses may be delivered to the left ventricle between the LV distal electrode 113 and the LV proximal electrode 117. In another example, unipolar pacing pulses may be delivered to the left ventricle, for example, between the LV distal electrode 113 and the can 209. The cardiac signal following the delivery of the pacing pulses may preferably be sensed using the LV proximal electrode 117 and the can 209.

In an example of right atrial pacing, bipolar pacing pulses may be delivered to the right atrium between the RA-tip electrode 156 and the RA-ring electrode 154. In another example, unipolar pacing pulses may be delivered to the right atrium, for example, between the RA-tip electrode 156 and the can electrode 209. For unipolar right atrial pacing, the preferred electrode combination for sensing cardiac signals following pacing for cardiac response classification comprises the RA-ring 154 to indifferent electrode.

In an example of left atrial pacing, bipolar pacing pulses may be delivered to the left atrium between the LA distal electrode 118 and the LA proximal electrode 115. In another example, unipolar pacing pulses may be delivered to the left atrium, for example, between the LA distal electrode 118 and the can electrode 209. The cardiac signal following the delivery of the pacing pulses and used for cardiac response classification may preferably be sensed using the RA-tip 156 to RA-ring 154 vector.

In one embodiment of the invention, a switching matrix 210 is coupled to the RA-tip 156, RA-ring 154, RV-tip 112, RV-coil 114, LV distal electrode 113, LV proximal electrode 117, SVC coil 116, LA distal electrode 118, LA proximal electrode 115, indifferent, and can 209 electrodes. The switching matrix 210 may be arranged to provide connections to various configurations of pacing and defibrillation electrodes. The outputs of the switching matrix 210 are coupled to an evoked response (ER) sensing circuit 237 that serves to sense and amplify cardiac signals detected between the selected combinations of electrodes. The detected signals are coupled through the ER amplifier 237 to a cardiac response classification processor 225. The cardiac response classification processor 225 includes circuitry configured to classify a cardiac response to a pacing stimulation, including, for example, classifying a captured response, a non-captured response, an intrinsic beat added to a non-captured response, and a fusion/pseudofusion response, in accordance with the invention.

Figure 2B:
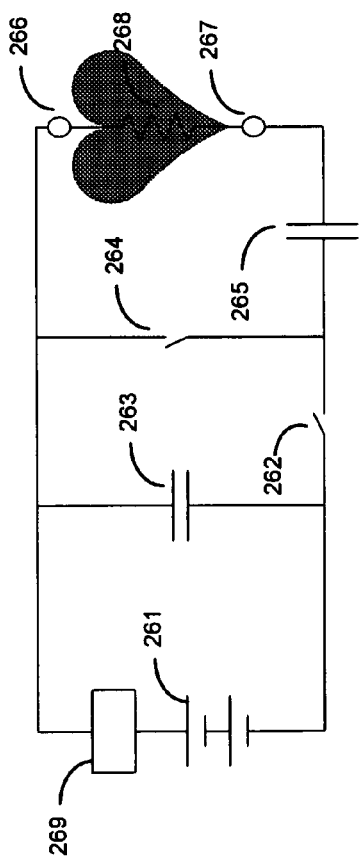
FIG. 2B is a schematic diagram of a circuit that may be used to generate pacing stimulations in accordance with embodiments of the invention.
Figure 2C:
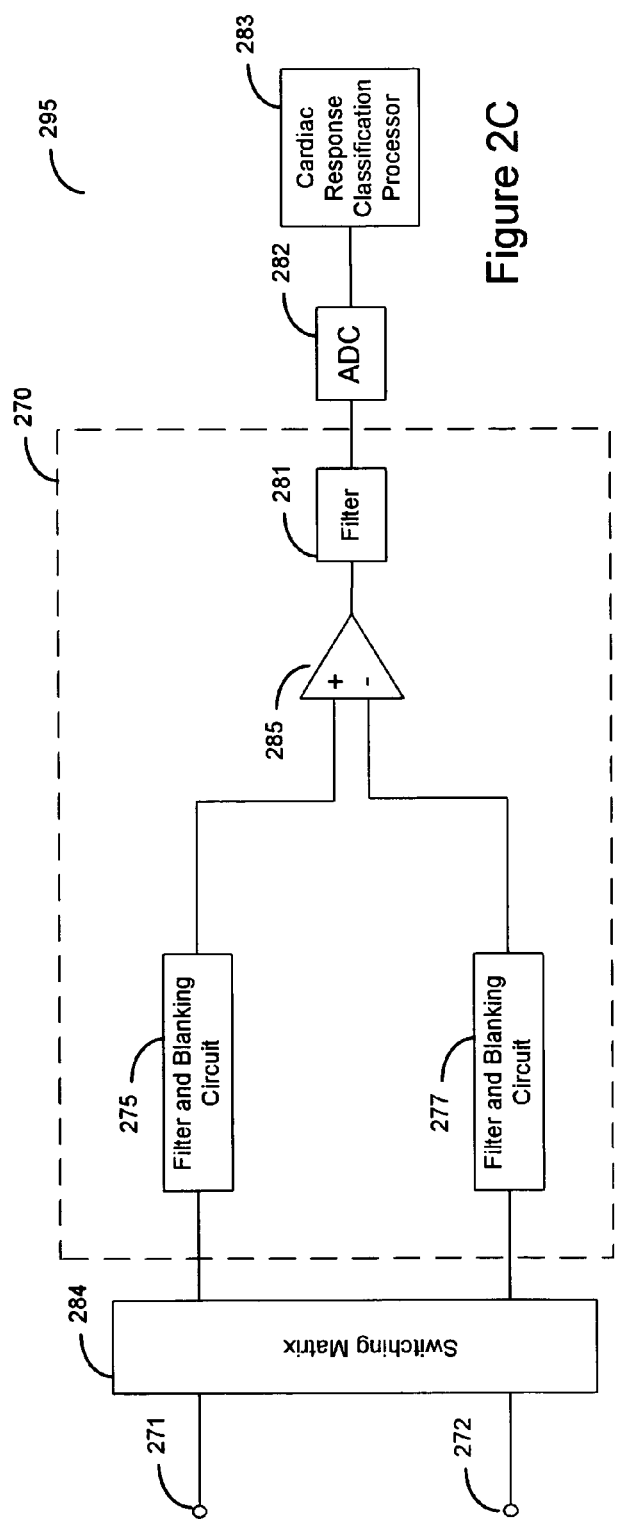
FIG. 2C is a schematic diagram of a circuit that may be used to sense a cardiac signal following the delivery of a pacing stimulation and to classify the cardiac response to the pacing stimulation according to embodiments of the invention.

FIGS. 2B and 2C illustrate more detailed examples of pacing and sensing circuitry, respectively, that may be used for cardiac pace/sense channels of a pacemaker in accordance with embodiments of the invention. It will be appreciated that the example pacing and sensing circuits illustrated in FIGS. 2B and 2C may be arranged to achieve the pacing and sensing vectors described above.

In example embodiments of the invention, the pacing circuit of FIG. 2B includes a power supply or battery 261, a first switch 262, a second switch 264, a pacing charge storage capacitor 263, coupling capacitor 265, and a pacer capacitor charging circuit 269 all of which are cooperatively operable under the direction of a controller of known suitable construction. The power supply or battery 261 is preferably the battery provided to power the pacemaker and may comprise any number of commercially available batteries suitable for pacing applications. The switches 262, 264 may be implemented using any number of conventionally available switches. The pacing capacitor charging circuit 269 includes circuitry to regulate the voltage across the pacing charge storage capacitor 263.

The pacing charge storage capacitor 263 may also comprise any number of conventional storage capacitors that can be Used to develop a sufficient pacing charge for stimulating the heart. The primary function of the coupling capacitor 265 is to block any DC signal from reaching the heart during pacing and additionally to attenuate the polarization voltage or "afterpotential" that results from pacing. The coupling capacitor 265 may have a capacitance, for example, in the range of about 2 microfarads to about 22 microfarads. Energy stored in the pacing charge storage capacitor 263 may be delivered to the heart 268 using various combinations of cardiac electrodes 266, 267, as described above.

FIG. 2C illustrates a block diagram of circuit 295 that may be used to sense cardiac signals following the delivery of a pacing stimulation and classify the cardiac response to the pacing stimulation according to embodiments of the invention. A switch matrix 284 is used to couple the cardiac electrodes 271, 272 in various combinations discussed above to the sensing portion 270 of the cardiac response classification circuit 295. The sensing portion 270 includes filtering and blanking circuitry 275, 277, sense amplifier 285, band pass filter 281, and analog to digital converter 282. The analog to digital converter 282 is coupled to a cardiac response classification processor 283.

A control system, e.g., the control system 220 depicted in FIG. 2A, is operatively coupled to components of the cardiac response classification circuit 280 and controls the operation of the cardiac response classification circuit 295, including the filtering and blanking circuits 275, 277. Following a blanking period of sufficient duration following delivery of the pacing stimulation, the blanking circuitry 275, 277 operates to allow detection of a cardiac signal responsive to the pacing stimulation. The cardiac signal is filtered, amplified, and converted from analog to digital form. The digitized signal is communicated to the cardiac response classification processor 283 which operates in cooperation with other components of the control system 220, FIG. 2A, including the template processor 241, FIG. 2A, to classify cardiac responses to pacing according to embodiments of the invention.

Figure 3:
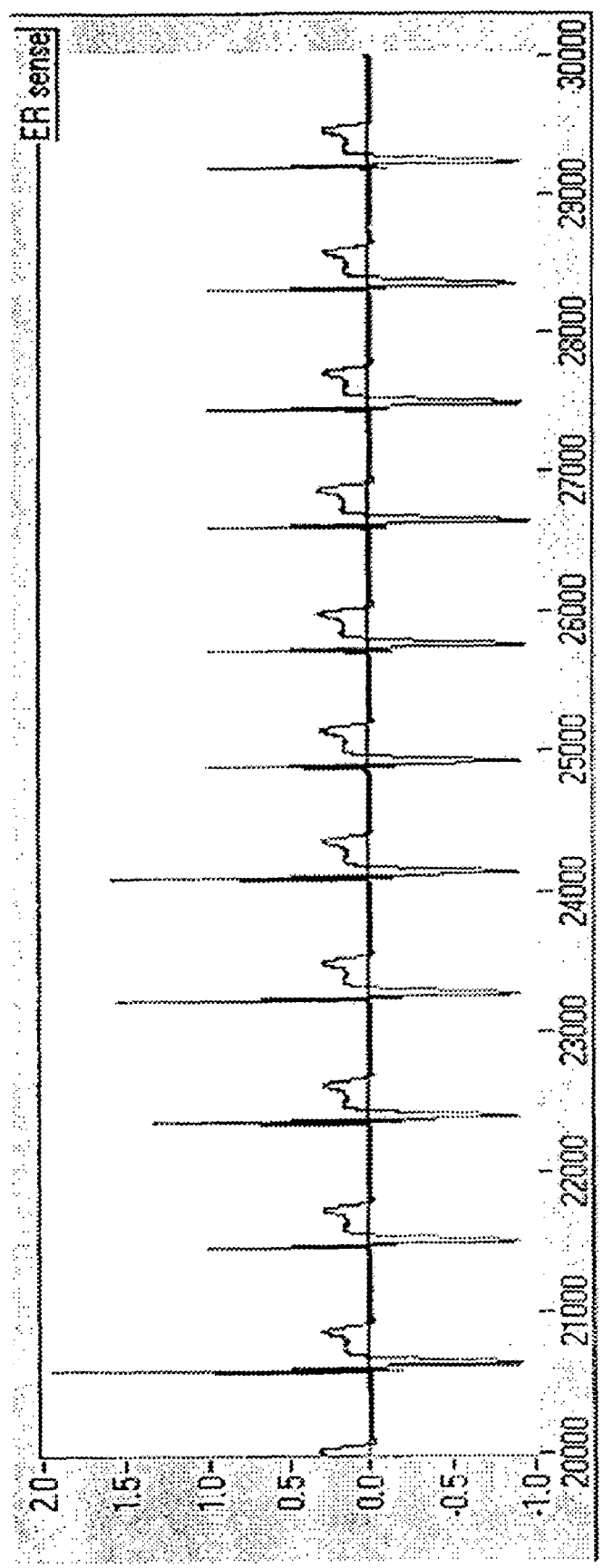
FIG. 3 is a graph illustrating a cardiac signal that indicates capture.
Figure 4A:
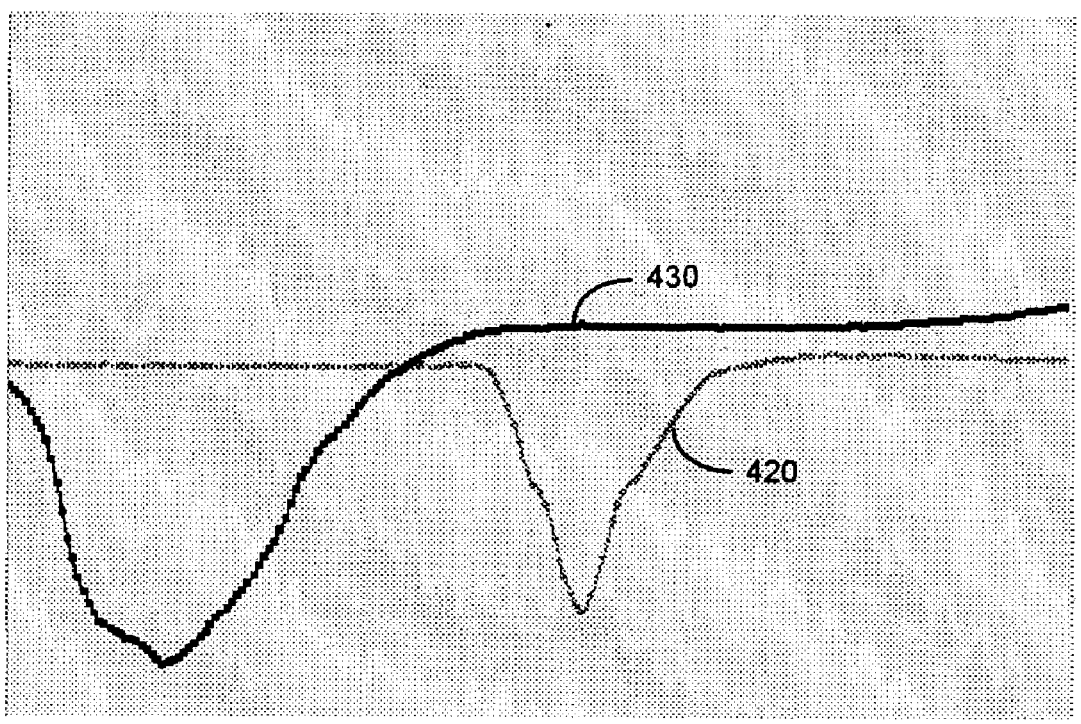
FIG. 4A illustrates superimposed graphs of a captured response and non-captured and intrinsic response when the pacing pulse is delivered on the RV rate channel and the cardiac signal following pacing is sensed on the RV shock channel in accordance with embodiments of the invention.

When pacing pulses delivered to the heart produce a depolarization wave in cardiac tissue resulting in a cardiac contraction, a captured response may be detected by examining the cardiac signal following the delivery of the pacing pulse. FIG. 3 is a graph illustrating the output of the sensing portion 270 of the cardiac response classification circuit 295 of FIG. 2C in which the cardiac signal consistently indicates capture following a sequence of pacing pulses. In this example, a pacing pulse is delivered to the heart using the RV-tip and RV-coil electrodes, also referred to herein as a right ventricular rate channel. The cardiac signal following a right ventricular pace is sensed using a RV-coil to SVC-coil+can sensing vector, also referred to herein as the shock channel. FIG. 4A provides superimposed graphs of a captured response 430 and non-captured and intrinsic response 420 when the pacing pulse is delivered on the RV rate channel and the cardiac signal following pacing is sensed on the RV shock channel.

Figure 4B:
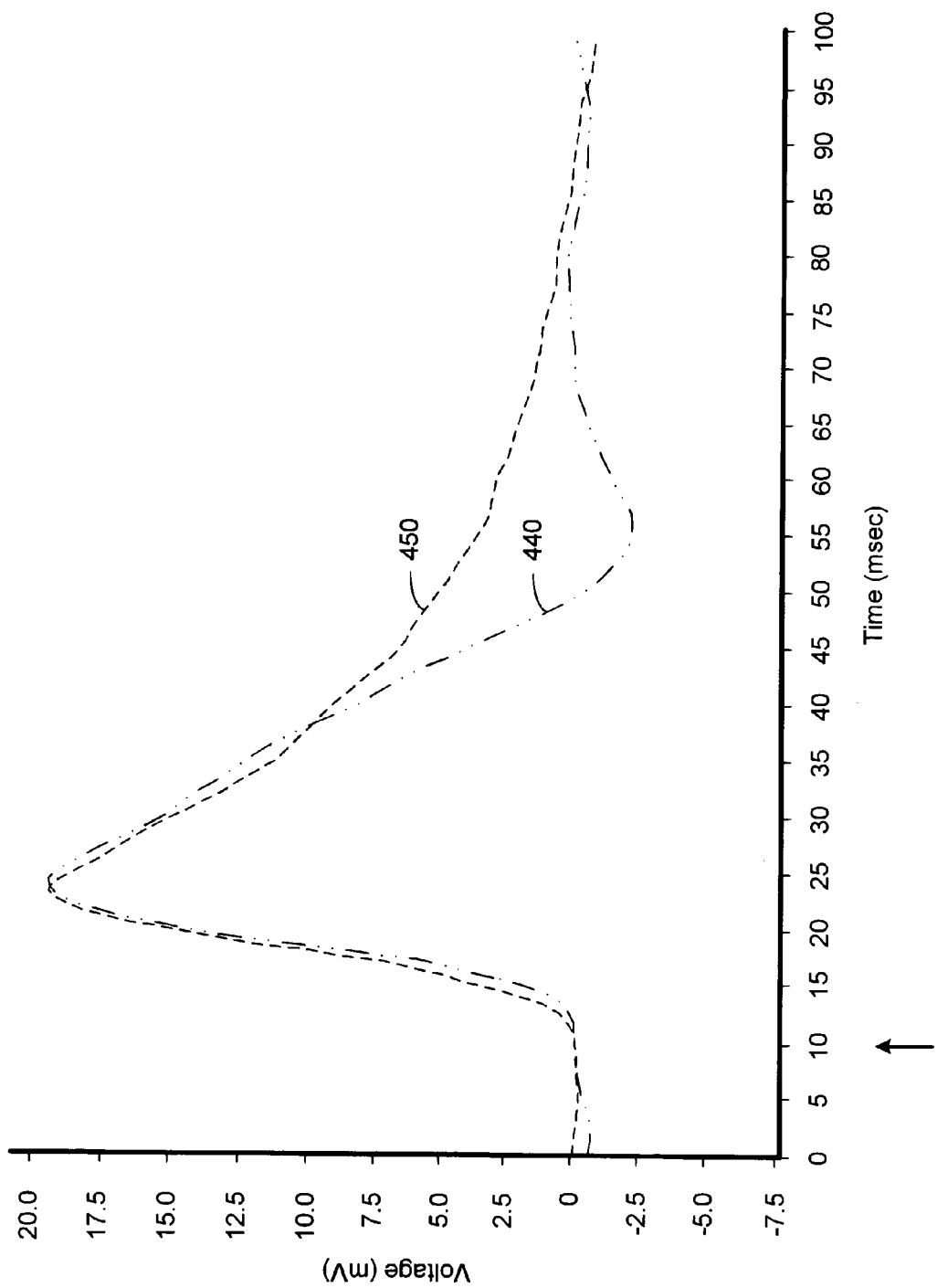
FIG. 4B illustrates superimposed graphs of a captured response and a non-captured response sensed using the same sensing vector in accordance with embodiments of the invention.

In another example, the same vector may be used to pace the heart chamber and sense the cardiac signal following the pace to classify the cardiac response. Pacing in the right ventricle may be accomplished using the pacing vector RV-tip to RV-ring, for example. FIG. 4B illustrates superimposed graphs of a captured response 440 and a non-captured response 450 sensed using that same vector, e.g., RA-tip to RA-ring.

Figure 5:
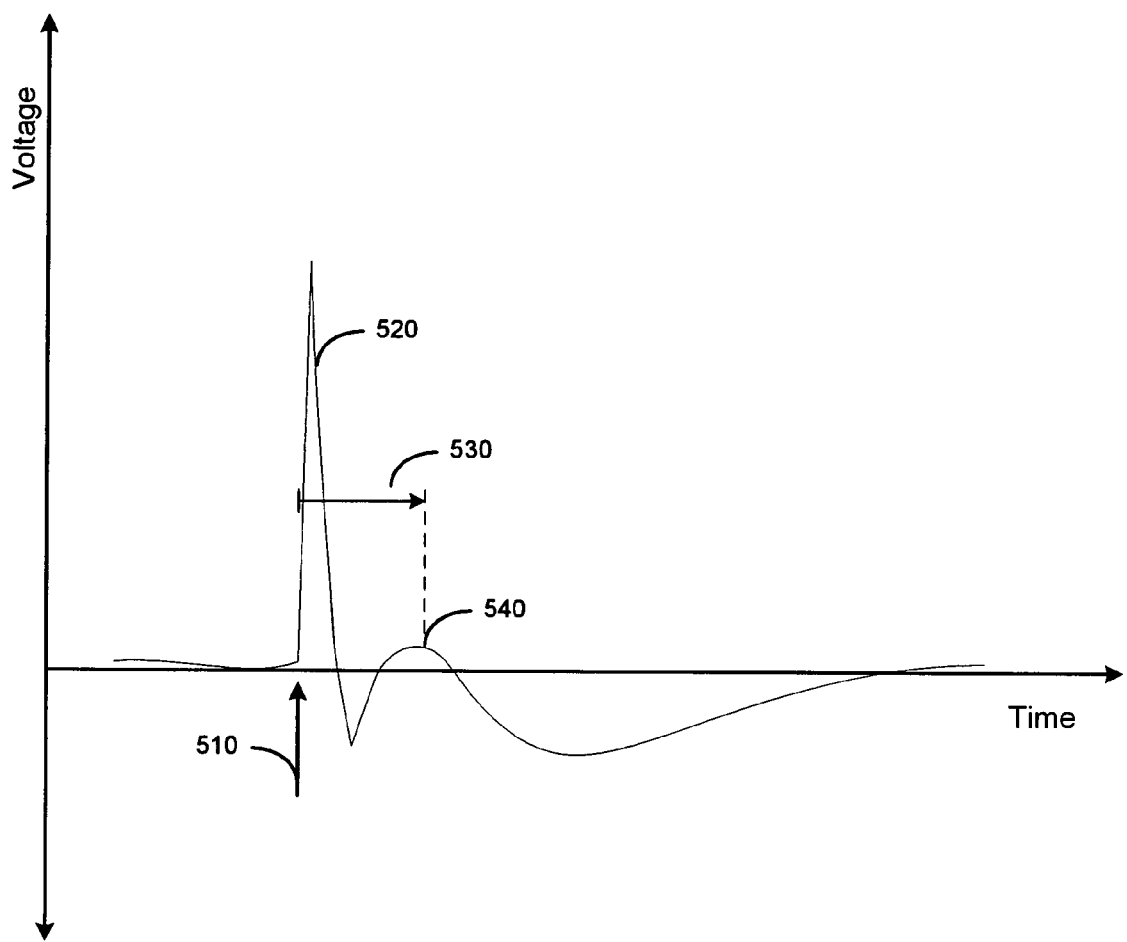
FIG. 5 is a graph illustrating a propagation delay of a cardiac signal sensed on a shock channel following a pacing pulse delivered on a rate channel.

As previously discussed, if a first vector, e.g., rate channel vector RV-tip to RV-coil, is used to deliver a pacing pulse and a second vector, e.g., shock channel vector RV-coil to SVC-coil or RV-coil to SVC-coil+can, is used to sense the cardiac signal responsive to the pacing pulse, the pacing artifact is separated from the evoked response due to a propagation delay from RV-tip to RV-coil. FIG. 5 is a graph illustrating a signal 520 sensed on a right ventricular (RV) shock channel vector following a pacing pulse 510 delivered on a rate channel. The cardiac signal 520 exhibits a propagation delay 530, for example, a propagation delay of about 55 ms, between the pacing pulse 510 and the portion of the cardiac signal indicating a captured response 540.

Figure 6:
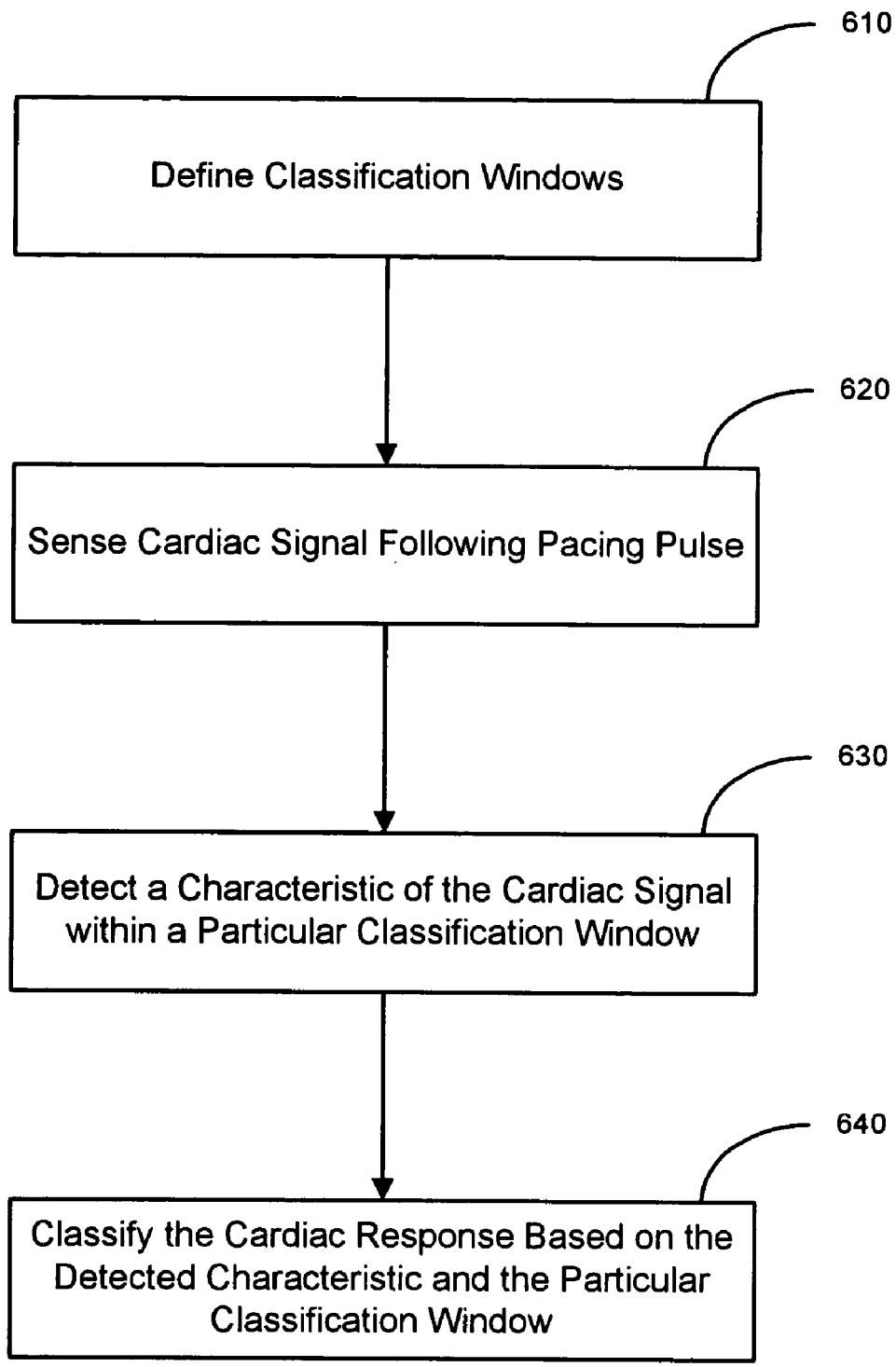
FIG. 6 is a flowchart illustrating a method of classifying a cardiac response to pacing using multiple classification windows in accordance with embodiments of the invention.

FIG. 6 is a flowchart illustrating a method of classifying a cardiac response to a pacing stimulation in accordance with embodiments of the invention. In this method the same electrode combination may be used for pacing and sensing, or a first electrode combination may be used for pacing and a second electrode combination may be used for sensing. If the same electrode combination is used for pacing and sensing, then pacing artifact cancellation may facilitate cardiac response classification. In accordance with this method, a plurality of response classification windows are defined 610 subsequent to delivery of a pacing pulse. A cardiac signal following the pacing pulse is sensed 620. One or more characteristics of the cardiac signal, for example, magnitude, slope or sequence of morphological feature points, are detected 630 in one or more particular classification windows of the plurality of classification windows. The cardiac response is classified 640 based on the one or more detected characteristics and the one or more particular classification windows in which the characteristic is detected. Although the flowchart of FIG. 6 describes classification of a cardiac response based on the detection of a characteristic of the cardiac signal within a particular classification window, any number of characteristics of the cardiac signal detected in any number of the classification windows may be used to classify the cardiac response according to the principles of invention.

Classification of a cardiac response to pacing may be accomplished using a multiple classification window approach. This approach may be applicable for pacing and sensing using the same vector or pacing and sensing using different vectors. Classification of a cardiac response to pacing in accordance with embodiments of the invention involves analyzing one or more features of the cardiac signal sensed following a pacing stimulation with respect to multiple classification windows. The cardiac response to pacing may be determined based on a feature of the cardiac signal and the classification window in which the feature is detected. Although in various examples provided herein, the classification windows are contiguous and non-overlapping, the classification windows may be overlapping and/or may involve a delay interval defined between classification windows.

Figure 7A:
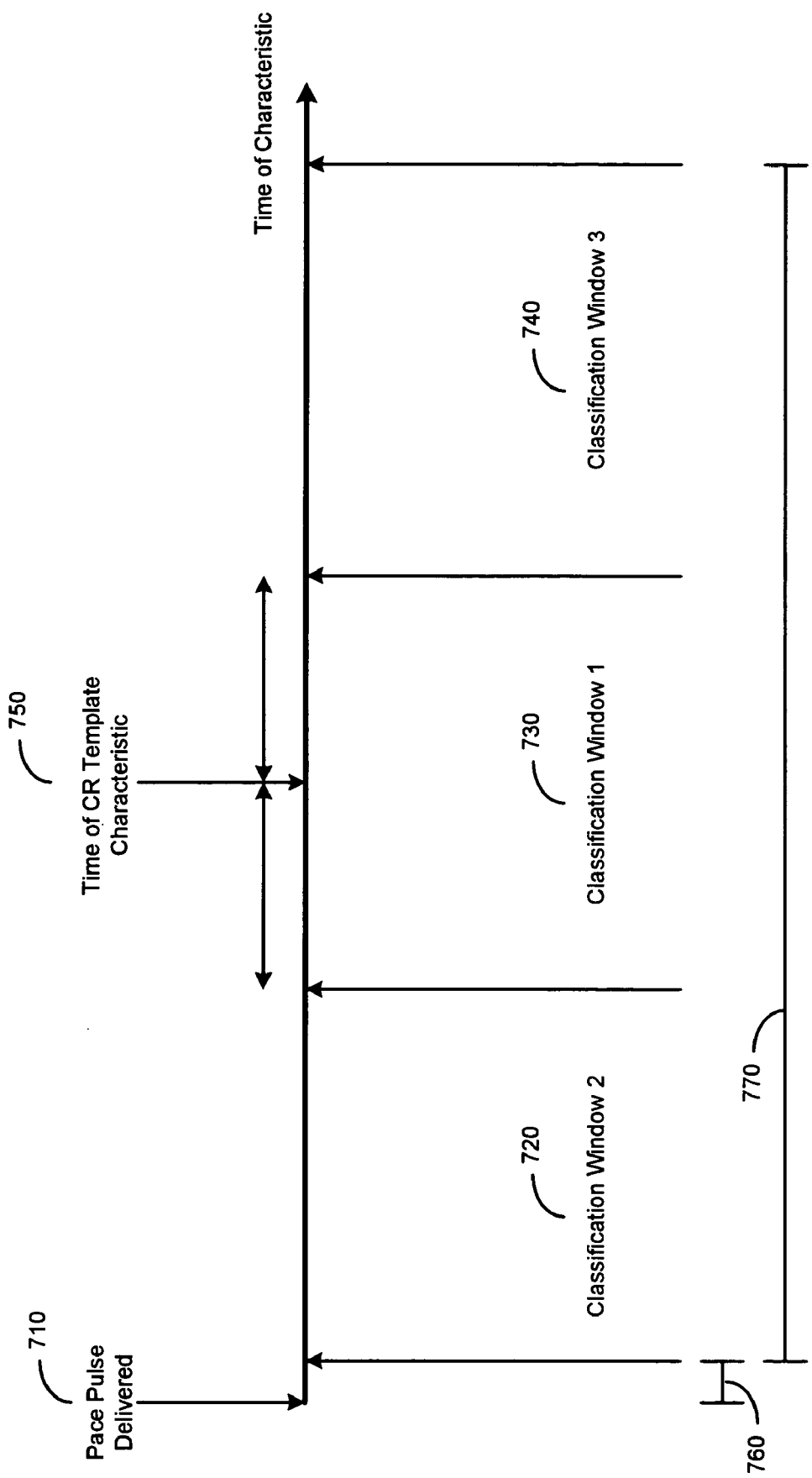
FIG. 7A illustrates establishment of a set of classification windows relative and subsequent to the pacing stimulation based on a captured response template characteristic in accordance with embodiments of the invention.

FIG. 7A illustrates the establishment of a set of classification windows relative and subsequent to the pacing stimulation. In this example, three classification windows 720, 730, 740 are established based on a selected characteristic of a captured response template. A captured response (CR) template exemplifies a waveform representative of a captured response as illustrated in FIGS. 4A and 4B. The CR template may be derived from a waveform that is produced when a pacing pulse captures the heart, and may include both the evoked response and the superimposed pacing artifact. A CR template may comprise, for example, a sequence of samples or feature points of a cardiac signal representing a captured response. Multiple cardiac response classification windows may be defined based on features of the CR template.

Initial generation of a CR template may be implemented by delivering pacing pulses to the heart at an energy greater than the capture threshold. Delivery of pacing pulses at a high energy level may be performed, for example, during a capture threshold test. A capture threshold test may involve pacing a selected heart chamber at an initially high energy level and ramping down the pacing energy until loss of capture is detected. Pacing pulses delivered early in the capture threshold test have energy levels exceeding the capture threshold, and produce cardiac signals indicative of captured beats. The pacing pulses may be delivered using a first vector and the cardiac signals following pacing may be sensed using a second vector. Alternatively, pacing and sensing may be implemented using the same vector. Cardiac signals representing one of more captured cardiac beats may be used to form the CR template.

Figure 7B:
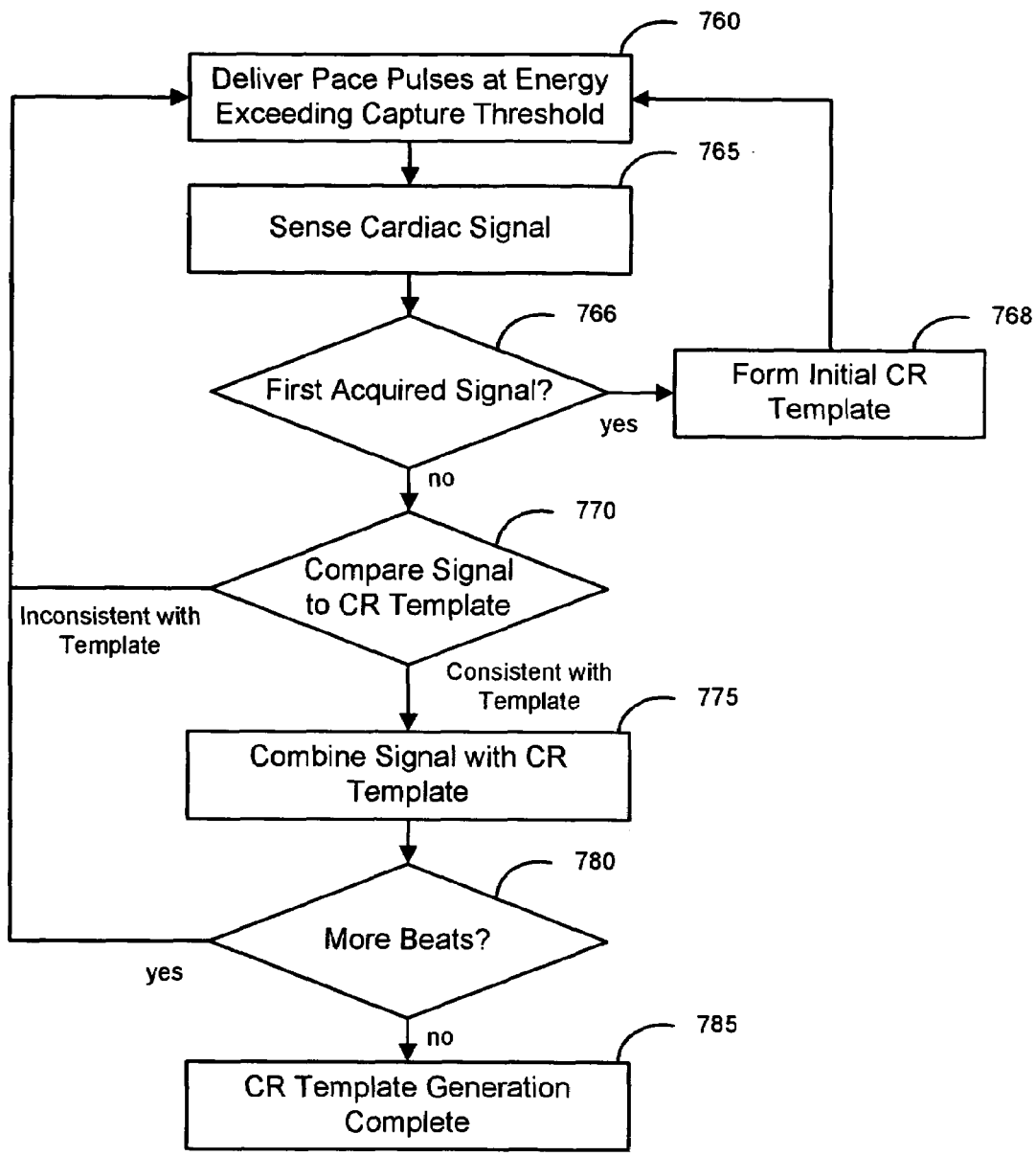
FIG. 7B is a flowchart illustrating a method of forming a captured response (CR) template in accordance with embodiments of the invention.

FIG. 7B is a flowchart illustrating a method of forming a CR template in accordance with embodiments of the invention. Pacing pulses are delivered 760 to a heart chamber at a pacing energy exceeding the capture threshold for the chamber. The cardiac signal following delivery of the pacing pulse is sensed 765. If the sensed cardiac signal is the first acquired signal 766, the cardiac signal is used 768 to form an initial CR template. If the sensed cardiac signal is not the first acquired signal 766, then the sensed cardiac signal is compared 770 to the existing CR template. If the sensed cardiac signal is consistent with 770 the CR template, then it is combined 775 with the CR template. A cardiac signal may be considered to be consistent with a template if the features, samples, or other morphological characteristics of the cardiac signal are determined to be sufficiently similar to the template features, samples, or morphological characteristics. If a cardiac signal is sufficiently similar to a template representative of a particular type of cardiac beat, then the cardiac signal may be classified as the particular type of beat. Various techniques may be used to compare a template and a cardiac signal, including the correlation techniques described herein.

In some implementations, a cardiac signal that is consistent 770 with the CR template may be combined with the CR template by averaging the cardiac signal and the CR template sample by sample, or by other averaging methods. In other implementations, different methods of combining the cardiac signal with the template may be used. If more beats are available 780 for CR template generation then the process of blocks 760-775 is repeated. If no more beats are available for CR template generation, then the CR template generation process is complete 785.

In one implementation, the comparison between an existing CR template and a sensed cardiac signal may be accomplished by calculating a correlation coefficient (CC) comparing the sensed cardiac signal and the CR template using a technique such as Correlation Waveform Analysis (CWA). According to this technique, a correlation coefficient (CC) may be calculated to compare the sensed cardiac signal to the CR template sample by sample. In one particular embodiment, Equation 1 is used to compute the CC between the samples of a cardiac signal sensed following a pacing pulse and the CR template samples.

$$CC = \frac{N\sum_{i=1}^{N} X_i Y_i - \left(\sum_{i=1}^{N} X_i\right)\left(\sum_{i=1}^{N} Y_i\right)}{\sqrt{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)}} \quad [1]$$

where, $X_i$ represents template N samples and $Y_i$ represents cardiac signal N samples in this illustrative example. Typically, the number of samples associated with each waveform or template is about 33 samples. If the correlation coefficient is greater than a predetermined value, for example, about 0.71, the cardiac signal is considered to represent a captured response signal and may be combined with the CR template.

In another implementation, features used to form an existing CR template and features of a sensed cardiac signal may be compared by calculating a feature correlation coefficient (FCC). The FCC may be determined, for example, using every fourth sample of the cardiac signal and the captured response template. For example, Equation 2, provided below, may be used to compute the FCC between selected CR template features and cardiac signal features:

$$FCC = \frac{\left(N\sum_{i=1}^{N} X_i Y_i - \left(\sum_{i=1}^{N} X_i\right)\left(\sum_{i=1}^{N} Y_i\right)\right)^2}{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)} \quad [2]$$

where, $X_i$ represents CR template N features and $Y_i$ represents beat N features. The sign of the numerator term is checked before squaring. If the numerator is negative, the beat is uncorrelated, and the remainder of the computation need not be performed.

If the FCC is greater than a predetermined value, for example 0.94, then the cardiac beat is correlated to the CR template. If the FCC is less than or equal to the predetermined value, then the cardiac beat is uncorrelated to the template.

The CR template may be periodically updated using cardiac signals classified as captured responses. Updating the CR template allows the CR template to adapt to slow variations in the patient's captured response over time. Updating the CR template may be accomplished by averaging, or otherwise combining, the samples or feature points of an existing CR template with corresponding samples or feature points of cardiac signals representing captured response beats.

If the CR template is updated, the classification windows based on CR template features or morphology may also be updated. For example, the timing of a classification window based on a CR template feature may be modified to accommodate an updated timing of the CR template feature. Further, the duration of one or more of the classification windows may be modified based on updated information with respect to the CR template morphology.

The classification windows may be adapted based on statistics of variability of the captured response morphology and/or intrinsic beat morphology, for example. In one implementation, captured responses detected during a capture threshold test and/or intrinsic beats may be used to form a statistical database for classification window adaptation. The timing and/or duration of one or more of the classification windows may be adjusted in response to the variability of the features of the captured response and/or the intrinsic response. For example, the timing and/or duration of a classification window may be set adaptively based on the statistics of variability of the timing of the intrinsic beat peak or the timing of the captured response peak.

In one implementation, a CR template may be formed or updated during a capture threshold test. The test may deliver pacing pulses to the heart at an initially high pacing energy and ramp down the pacing energy over a series of pulses until a loss of capture is detected. A CR template may be formed or updated using the cardiac signals associated with captured responses following delivery of high energy pace pulses to the heart during capture threshold testing.

Returning to FIG. 7A, establishment of classification windows used to classify a cardiac signal following a pacing pulse is further described. In this example, classification windows may be established based on a feature or features of the captured response (CR) template. As illustrated in FIG. 7A, a first classification window 730 may be established based on the time 750 of a selected characteristic of a captured response (CR) template. In one example, the first classification window 730 is established based on the timing of the peak of the CR template, although other characteristics such as slope, curvature, amplitude, rise time or fall time may be used. The first classification window 730 represents a time interval defined in relation to the timing of the selected characteristic of the CR template 750 from a pacing stimulation 710. In the example illustrated in FIG. 7A, the first classification window 730 comprises a time interval, e.g., a time interval of about 20 ms, centered at the time 750 of the selected CR template characteristic with respect to the time of the delivery of the pacing pulse.

In this example, a second classification window 720 may be defined subsequent to the time 710 of the delivery of the pacing pulse and prior to the beginning of the first classification window 730. A third classification window 740 may be defined following the end of the first classification window 730.

The classification windows may be defined for example, following a blanking period 760 that is initiated subsequent to the delivery 710 of the pacing pulse. The blanking period 760 may comprise an interval of less than about 40 ms, or other value, for example. The first, second and third classification windows may comprise a total time interval of less than about 200 ms, for example.

FIGS. 7A and 7B and the associated discussion illustrate methods of defining classification windows using a captured response (CR) template characteristic, e.g., the CR template peak in accordance with embodiments of the invention. Such a technique may be particularly useful if different pacing and sensing vectors are used to reduce the effect of the pacing artifact. Classification of a cardiac response using multiple classification windows may be enhanced using cancellation of the pacing artifact, particularly if the same vector is used for pacing and sensing.

Figure 7C:
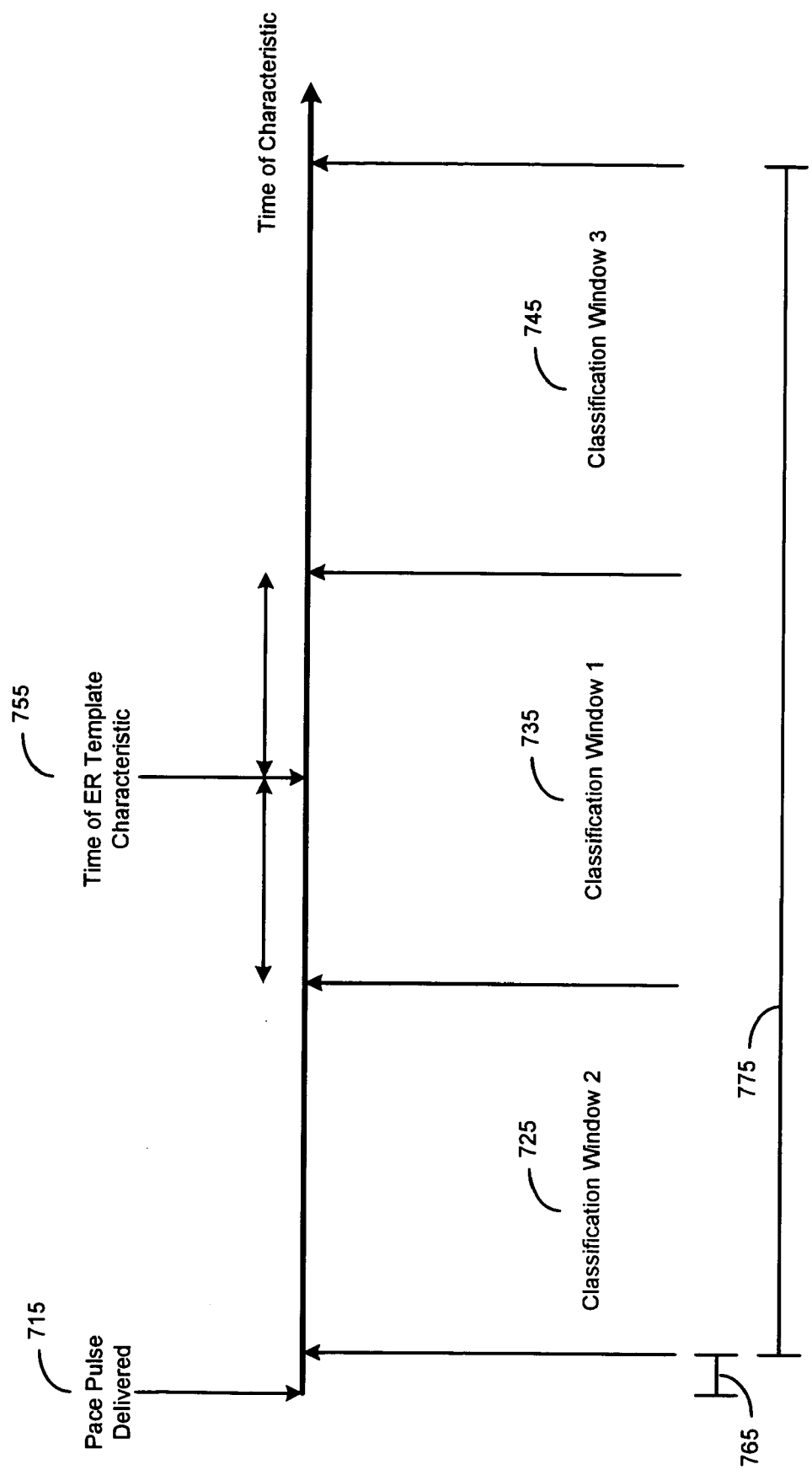
FIG. 7C illustrates establishment of a set of classification windows relative and subsequent to the pacing stimulation based on an evoked response template characteristic in accordance with embodiments of the invention.
Figure 7D:
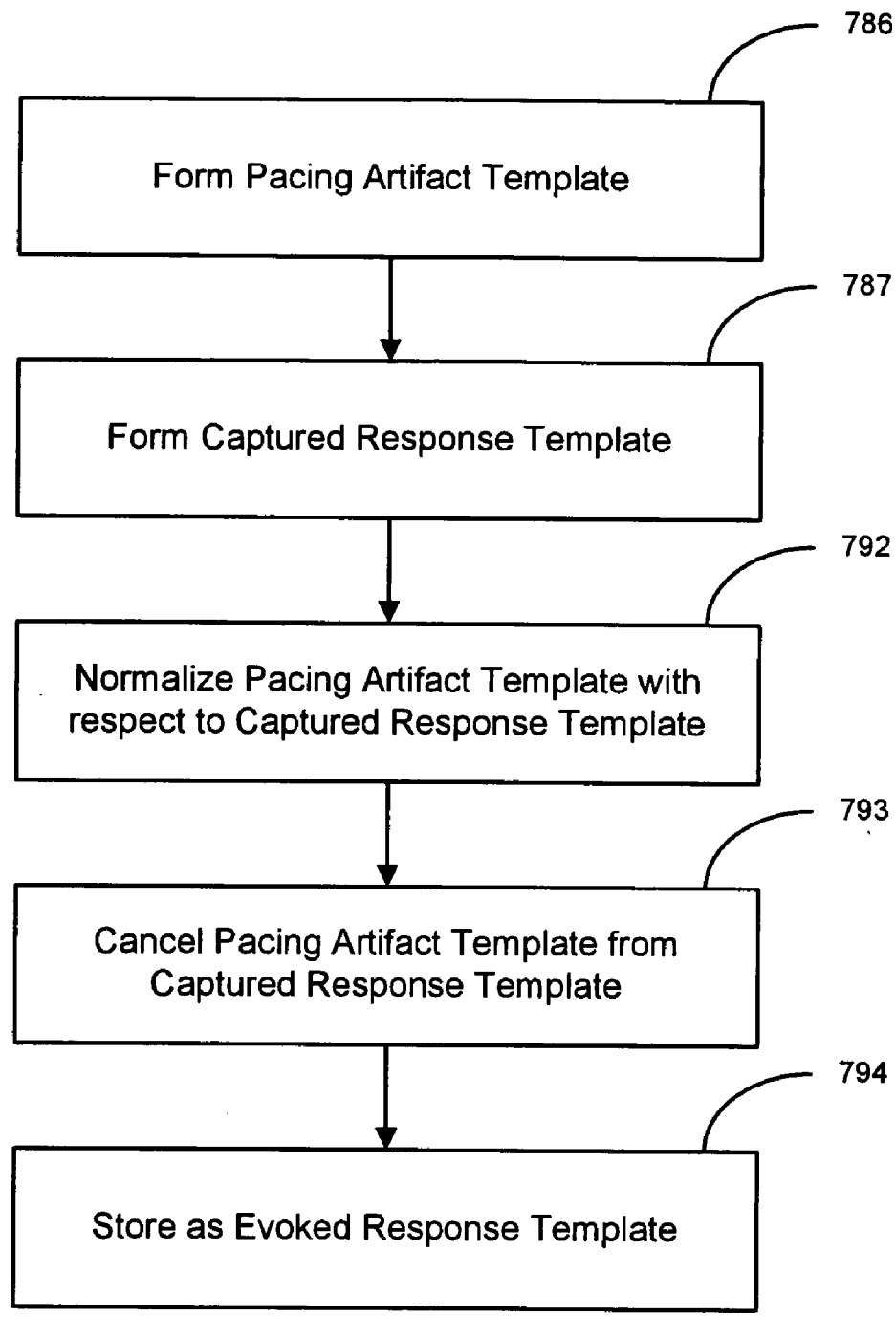
FIG. 7D is a flowchart illustrating a method of providing an evoked response template for use in cardiac response classification in accordance with embodiments of the invention.

FIGS. 7C and 7D illustrate a method of cardiac response classification involving cancellation of the pacing artifact from the sensed cardiac signal in accordance with various embodiments of the invention. According to this approach, a pacing artifact template representative of the pacing artifact is determined. The captured response template may be determined as described above. The pacing artifact template is then cancelled from the captured response template. Cancellation of the pacing artifact template from the captured response template defines a template representative of the evoked response (ER), i.e., the portion of the cardiac signal representing the evoked response without the superimposed pacing artifact. Multiple cardiac response classification windows may be defined based on a feature or features of the ER template.

For a paced beat, classification of a cardiac response to the pacing stimulation involves canceling the pacing artifact template from the cardiac signal sensed following a pacing pulse. One or more features of the pacing artifact cancelled signal may be analyzed with respect to the multiple classification windows. The cardiac response may be determined based on a feature of the pacing artifact cancelled cardiac signal and the classification window in which the feature is detected.

As illustrated in FIG. 7C, a first classification window 735 may be established based on the time 755 of a selected characteristic of an evoked response (ER) template. In one example, the first classification window 735 is established based on a peak of the ER template, although other characteristics such as slope, curvature, amplitude, rise time or fall time may be used. The first classification window 735 represents a time interval defined in relation to the timing of the selected characteristic of the ER template 755 from a pacing stimulation 715. In the example illustrated in FIG. 7C, the first classification window 735 comprises a time interval, e.g., a time interval of about 20 ms, centered at the time 755 of the selected ER template characteristic.

In this example, a second classification window 725 is established subsequent to the time 715 of the delivery of the pacing pulse and prior to the beginning of the first classification window 735. A third classification window 745 may be established following the end of the first classification window 735.

FIG. 7D is a flowchart illustrating a method of providing an evoked response template for use in cardiac response classification in accordance with embodiments of the invention. In this example, the heart is stimulated by pace pulses having a voltage greater than the capture threshold. The resultant captured cardiac responses are sensed and averaged to form a captured response template. A pacing artifact template is subtracted or otherwise cancelled from the captured response template to produce an evoked response template.

Turning to the flowchart of FIG. 7D, a pacing artifact template is provided at block 786. Generation of the pacing artifact template is described in connection with FIG. 7E below. A captured response template may be determined 787 by delivering a predetermined number of pace pulses at a pacing voltage greater than the capture threshold as described in connection with FIG. 7B above. The pacing artifact template may be normalized 792 with respect to the captured response template. Following normalization, the pacing artifact template is canceled from the captured response template 793. For example, the pacing artifact template may be canceled by subtracting the pacing artifact template from the captured response template sample by sample. The result of the subtraction of the pacing artifact template from the captured response template may be stored 794 as an evoked response template. The evoked response template may be used in subsequent cardiac response classification procedures.

In another embodiment, the pacing artifact template may be normalized and canceled from a number of captured response beats. The pacing artifact template canceled beats may then be averaged to produce the evoked response template.

Figure 7E:
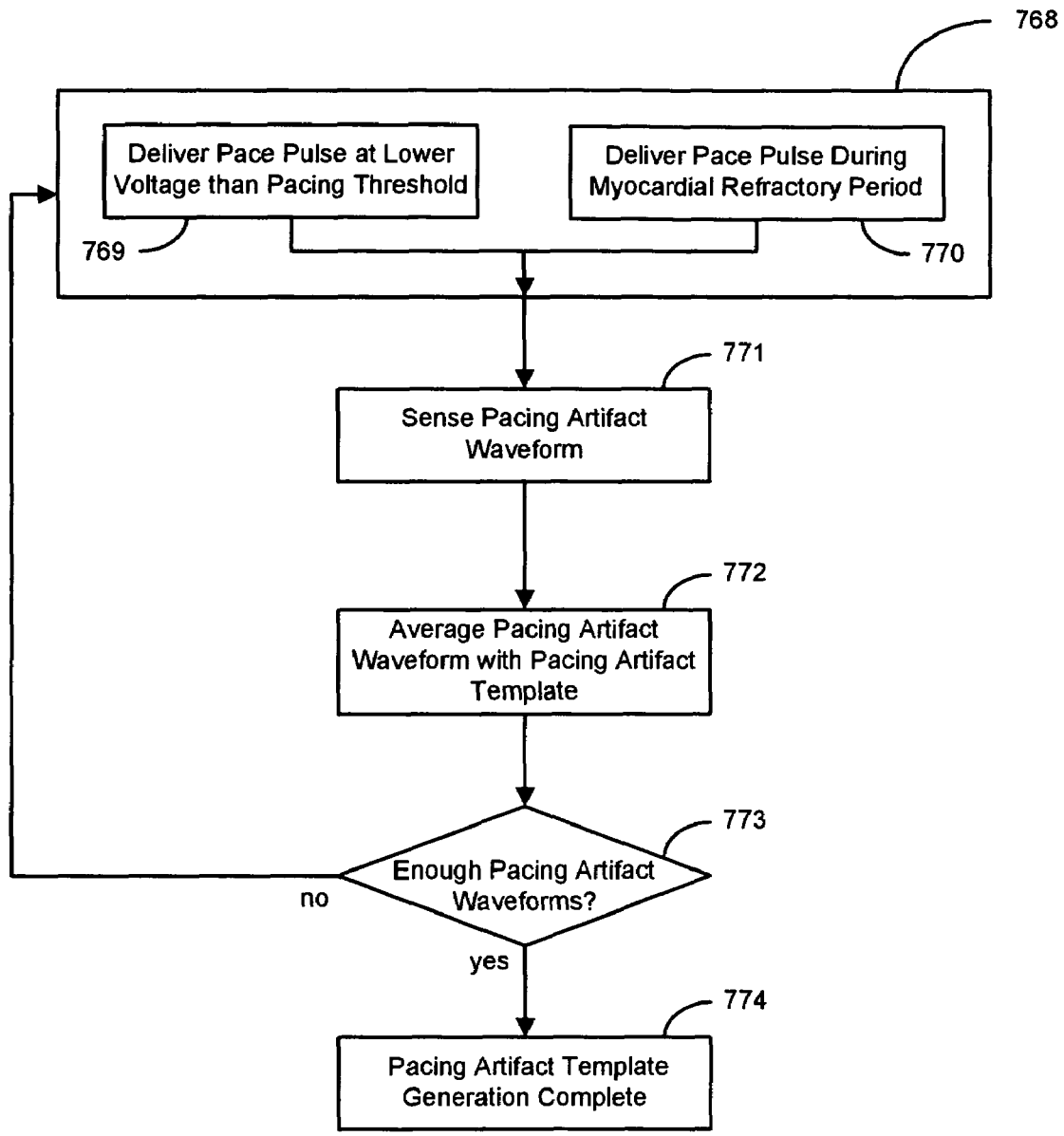
FIG. 7E is a flowchart illustrating a method of acquiring a pacing artifact template in accordance with an embodiment of the invention.

FIG. 7E illustrates a method of generating a pacing artifact template according to embodiments of the invention. In the exemplary embodiment illustrated by FIG. 7E, a number of pace pulses are delivered 768 to generate pacing artifact waveforms. The pace pulses are delivered in such a way that capture does not occur. The resultant cardiac signal may represent a relatively pure pacing artifact waveform without a superimposed evoked response. Pacing artifact signals without an associated evoked response may be produced by delivering 769 pace pulses at an energy level lower than the pacing threshold. Alternatively, the pace pulses may be delivered 770 during a myocardial refractory period. The myocardial refractory period represents a time when the heart tissue is recovering from a previous cardiac beat. A pace pulse delivered during the myocardial refractory period typically does not produce an evoked response in the heart tissue, thus a pacing artifact waveform may be acquired.

Following delivery 768 of a pace pulse using either of the above methods described in connection with blocks 769 or 770, a pacing artifact waveform is sensed 771. The pacing artifact waveform may be averaged with previously acquired pacing artifact waveforms 772, if any. The process of generating a pace pulse and detecting the resultant pacing artifact waveform 768-772 may be repeated until a predetermined number of pacing artifact waveforms has been acquired 773. When a sufficient number of pacing artifact waveforms has been acquired 773, the average pacing artifact waveform is stored 774 as the pacing artifact template.

The pacing artifact may exhibit small variations in morphology with respect to pace pulse amplitude. Accordingly, the use of multiple pacing artifact templates corresponding to various pace pulse amplitudes may provide a more thorough cancellation of the pacing artifact over a range of pace pulse amplitudes, e.g., as used in a pacing threshold test. The method illustrated in FIG. 7E may be applied to generate pacing artifact templates for each pacing pulse amplitude of interest.

Alternatively, or additionally, a set of two or more pacing artifact templates may be generated, wherein a particular pacing artifact template characterizes the pacing artifact associated with a small range of pace pulse amplitudes. A pacing artifact template for a pace pulse range can be formed by combining pacing artifact waveforms from various pace pulse amplitudes within the range using, for example, an averaging operation. The pacing artifact template for a pace pulse range may also be formed by selecting a pacing artifact waveform at a single pace pulse amplitude, e.g., a pacing artifact waveform for a pulse amplitude near the center of the range to be characterized. The set of pacing artifact templates correspond to the entire pace pulse amplitude range to be evaluated.

The artifact waveform measurement may be accomplished during the refractory period of the myocardium. Pace pulses delivered during the refractory period produce pacing artifact waveforms without the evoked response components. The timing of the pace pulse delivered for pacing artifact measurement in the myocardial refractory period should be selected to be before the vulnerable period of the myocardium to avoid pro-arrhythmia, and after the deflections from the myocardial response from the previous cardiac event in the chamber have passed, e.g., 80 ms after the preceding cardiac event.

Processes for CR template formation, ER template formation, and pacing artifact template formation are described in commonly owned U.S. Pat. No. 7,191,004 and U.S. Pat. No. 7,162,301, both of which are incorporated herein by reference.

Figure 8A:
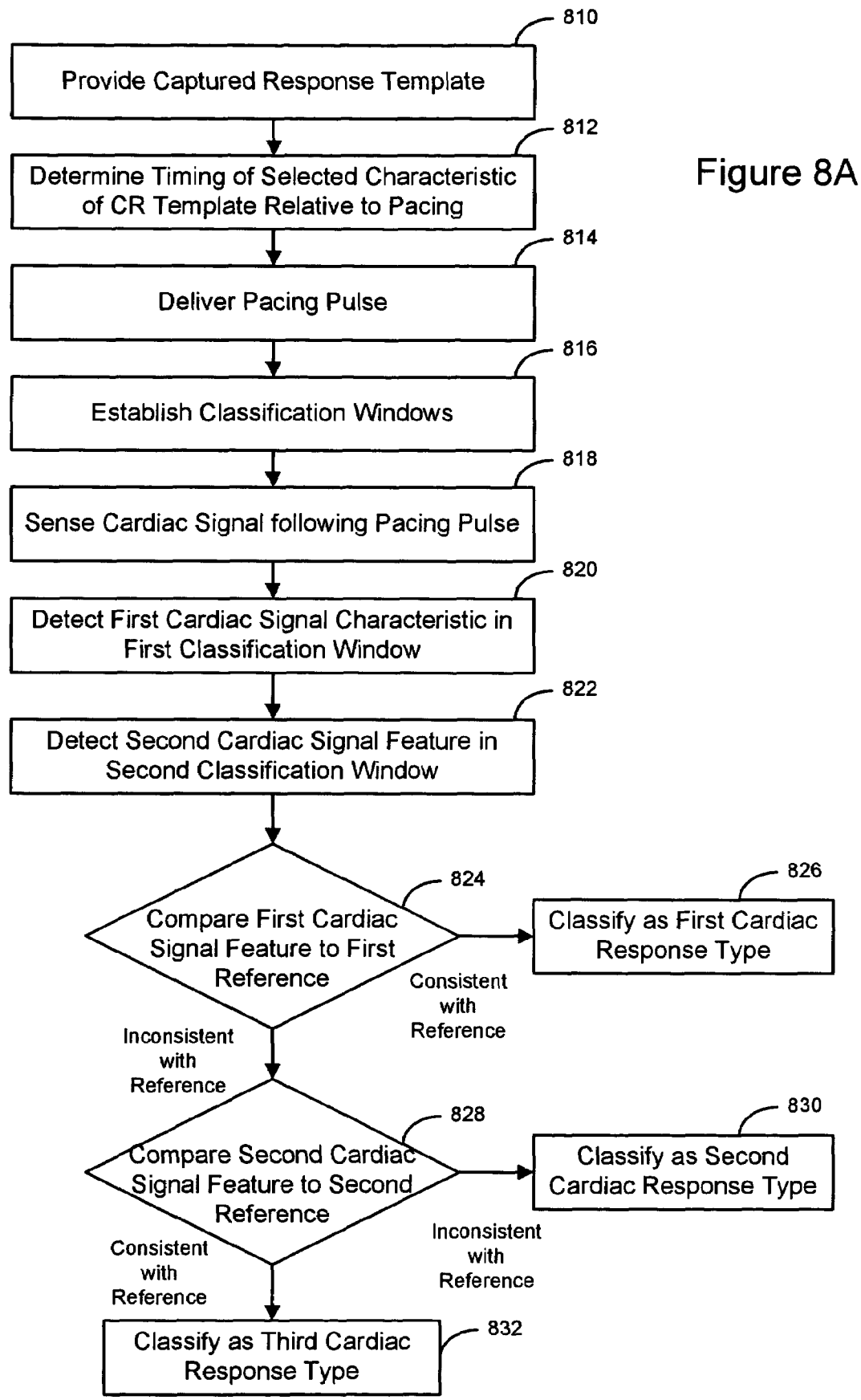
FIG. 8A is a flowchart illustrating a method of cardiac response classification utilizing a captured response (CR) template to define multiple classification windows in accordance with embodiments of the invention.
Figure 9:
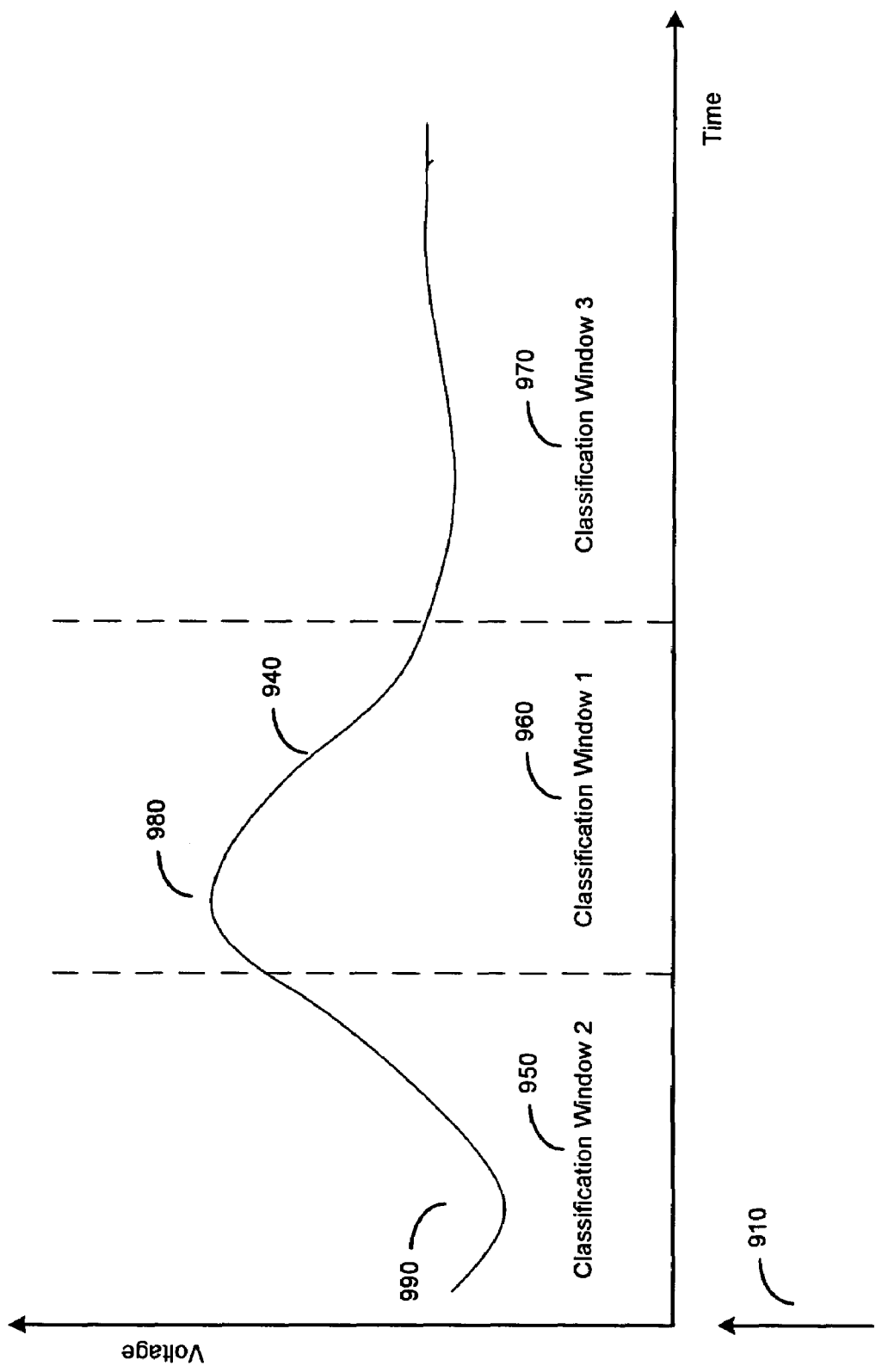
FIG. 9 is a diagram illustrating a cardiac signal sensed within multiple classification windows established following a pacing pulse in accordance with embodiments of the invention.

The flowchart of FIG. 8A illustrates a method of cardiac response classification utilizing a captured response (CR) template to define multiple classification windows according to embodiments of the invention. A captured response template is provided 810, for example, using a technique such as the one described above. The timing of a selected characteristic of the CR template is determined 812 relative to a pacing stimulation. A pacing pulse is delivered 814 and cardiac response classification windows are established 816 based on the timing of the selected CR template characteristic, as illustrated in FIG. 9. A cardiac signal following the pacing pulse is sensed 818. A first cardiac signal characteristic is detected 820 in the first classification window and a second cardiac signal characteristic may be detected 822 in the second classification window.

The first characteristic is compared 824 to a first reference. If the first characteristic is consistent with the first reference, then the cardiac response is classified 826 as a first type of response. If the first characteristic is inconsistent with the reference, then the second characteristic may be checked.

The second characteristic is compared to a second reference 828. If the second characteristic is inconsistent with the second reference, the cardiac signal is classified 830 as a second type of response. If the second characteristic is consistent with the second reference, then the cardiac signal is classified as a third type of response 832.

This example is further illustrated by the graph of FIG. 9. A plurality of classification windows 950, 960, 970 are established relative to a pacing pulse 910 based on the timing of a selected characteristic of the CR template. For example, the selected characteristic may comprise an extrema point, slope, curvature or other morphological feature characteristic of the CR template. A cardiac signal 940 following the pacing pulse is illustrated with respect to three established classification windows 950, 960, 970. A first characteristic 980, in this example, a positive peak, is detected in the first classification window 960. A second characteristic, e.g., negative peak 990 is detected in the second classification window 950. The first and the second characteristics 980, 990 may be compared to references and the cardiac response classified as described in connection with the flowchart of FIG. 8A.

Figure 8B:
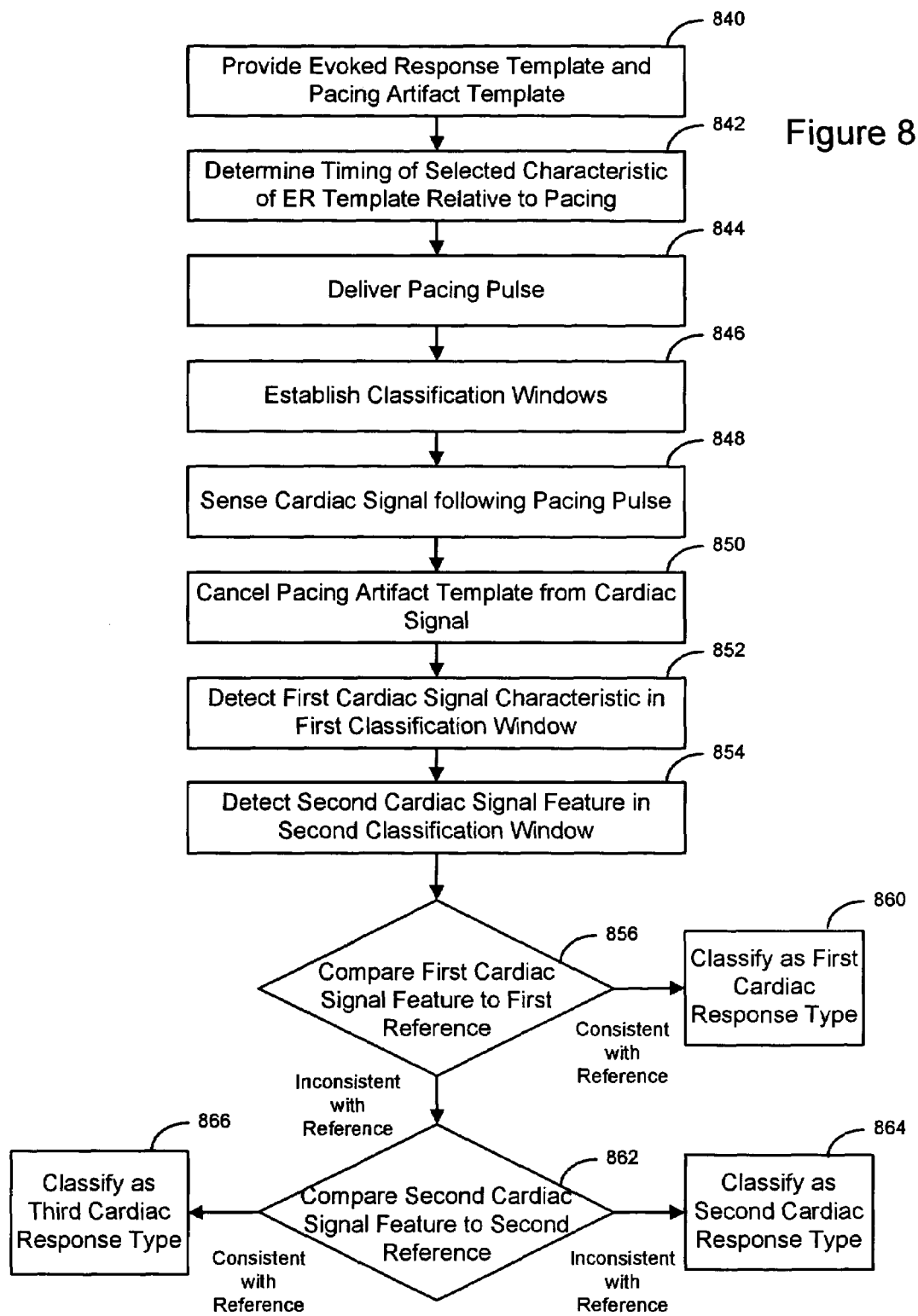
FIG. 8B is a flowchart illustrating a method of cardiac response classification using an evoked response template to define multiple classification windows in accordance with embodiments of the invention.

The flowchart of FIG. 8B illustrates a method of cardiac response classification using an evoked response template to define multiple classification windows in accordance with embodiments of the invention. An evoked response (ER) template and a pacing artifact template are provided 840, for example, using the techniques described above. The timing of a selected characteristic of the ER template is determined 842 relative to a pacing stimulation. A pacing pulse is delivered 844 and first and second classification windows are established 846 based on the timing of the selected ER template characteristic. A cardiac signal following the pacing pulse is sensed 848. The pacing artifact template is subtracted from the sensed cardiac signal 850. Using the pacing artifact cancelled cardiac signal, a first cardiac signal characteristic is detected 852 in the first classification window and a second cardiac signal characteristic is detected 854 in the second classification window.

The first characteristic is compared 856 to a first reference. If the first characteristic is consistent with the first reference, then the cardiac response is classified 860 as a first type of response. If the first characteristic is inconsistent with the reference 856, then the second characteristic is checked 862.

The second characteristic is 862 compared to a second reference. If the second characteristic is inconsistent 862 with the second reference, the cardiac signal is classified 864 as a second type of response. If the second characteristic is consistent 862 with the second reference, then the cardiac signal is classified as a third type of response 866.

Figure 10:
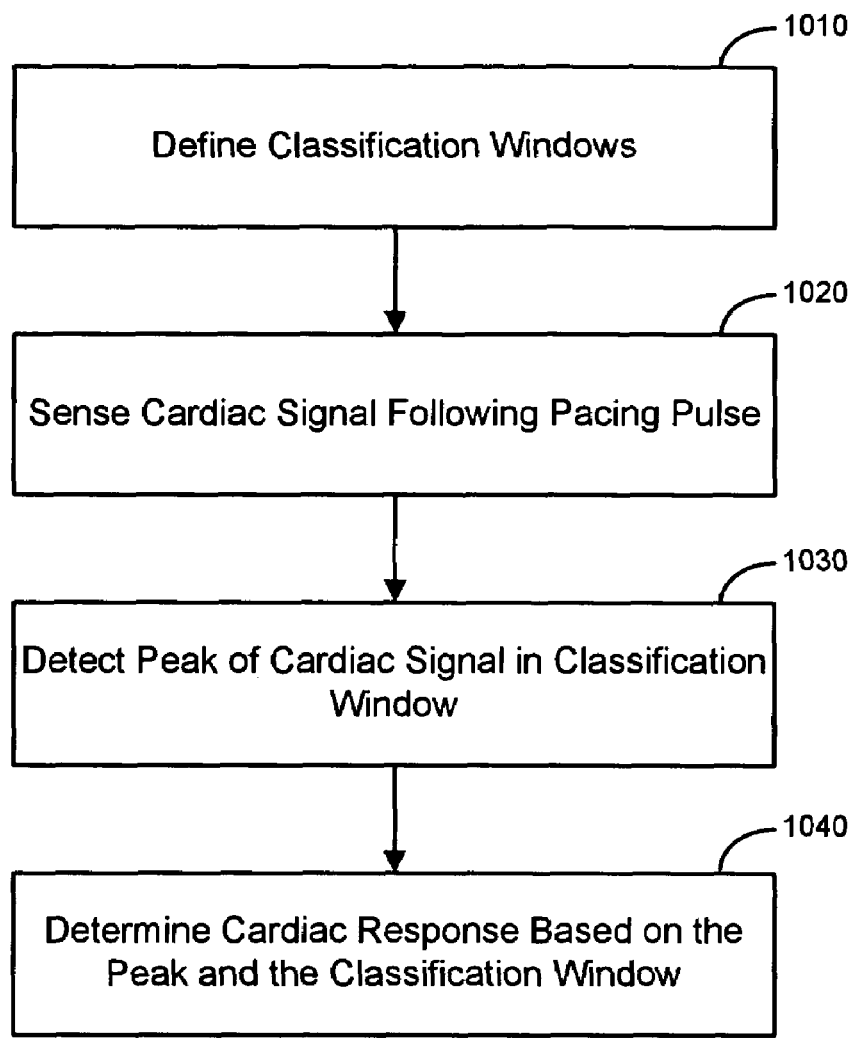
FIG. 10 is a flowchart illustrating a method for performing cardiac response classification in accordance with embodiments of the invention.

The cardiac response classification processes described herein may be implemented in an autocapture process wherein capture of the heart is verified on a beat-by-beat basis during pacing. If a pacing stimulation does not produce a captured response, a variety of interventions may be effected, including, for example, delivering a back-up pacing stimulation at a higher energy level and/or initiating a capture threshold test to determine the capture threshold of the cardiac tissue. In accordance with embodiments of the invention, a method for performing cardiac response classification that is particularly suitable for implementation in an autocapture process is illustrated in the flowchart of FIG. 10. Although the process described in FIG. 10 is described in connection with an autocapture procedure, the process may be advantageously applied in other procedures in connection with cardiac response classification.

Classification windows are defined 1010 based on the timing of the peak of the CR template. A cardiac signal following a pacing stimulation is sensed 1020. The peak of the sensed cardiac signal is detected 1030 in one of the classification windows. Classification of the cardiac response is performed 1040 based on the amplitude of the peak and the particular classification window in which the peak is sensed.

Figure 11:
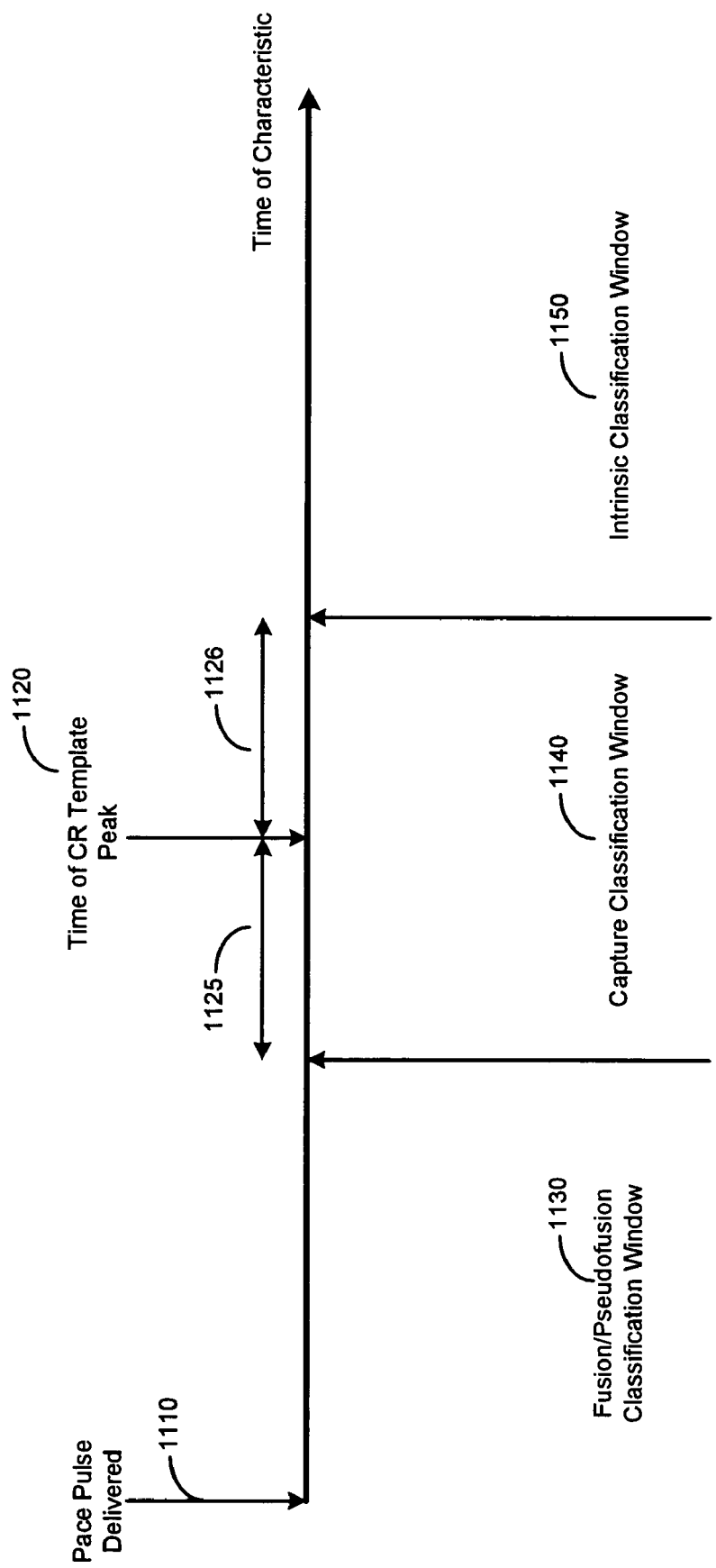
FIG. 11 is a diagram illustrating fusion, capture, and non-capture plus intrinsic response classification windows in accordance with embodiments of the invention.

FIG. 11 is a graph illustrating the implementation of classification windows that may be established in connection with the method of FIG. 10. In this example, three classification windows 1130, 1140, 1150 are established based on the timing of the peak of the CR template 1120 relative to the timing of the delivery of the pacing stimulation 1110. In this example, a first classification window 1130 is associated with a fusion/pseudofusion response, the second window 1140 is associated with a captured response, and the third window 1150 is associated with intrinsic beats. The second classification window 1140 may be centered about the timing of the CR template peak 1120 and includes predetermined intervals before 1125 and after 1126 the CR template peak 1120, e.g., intervals of about 10 ms.

Figure 12:
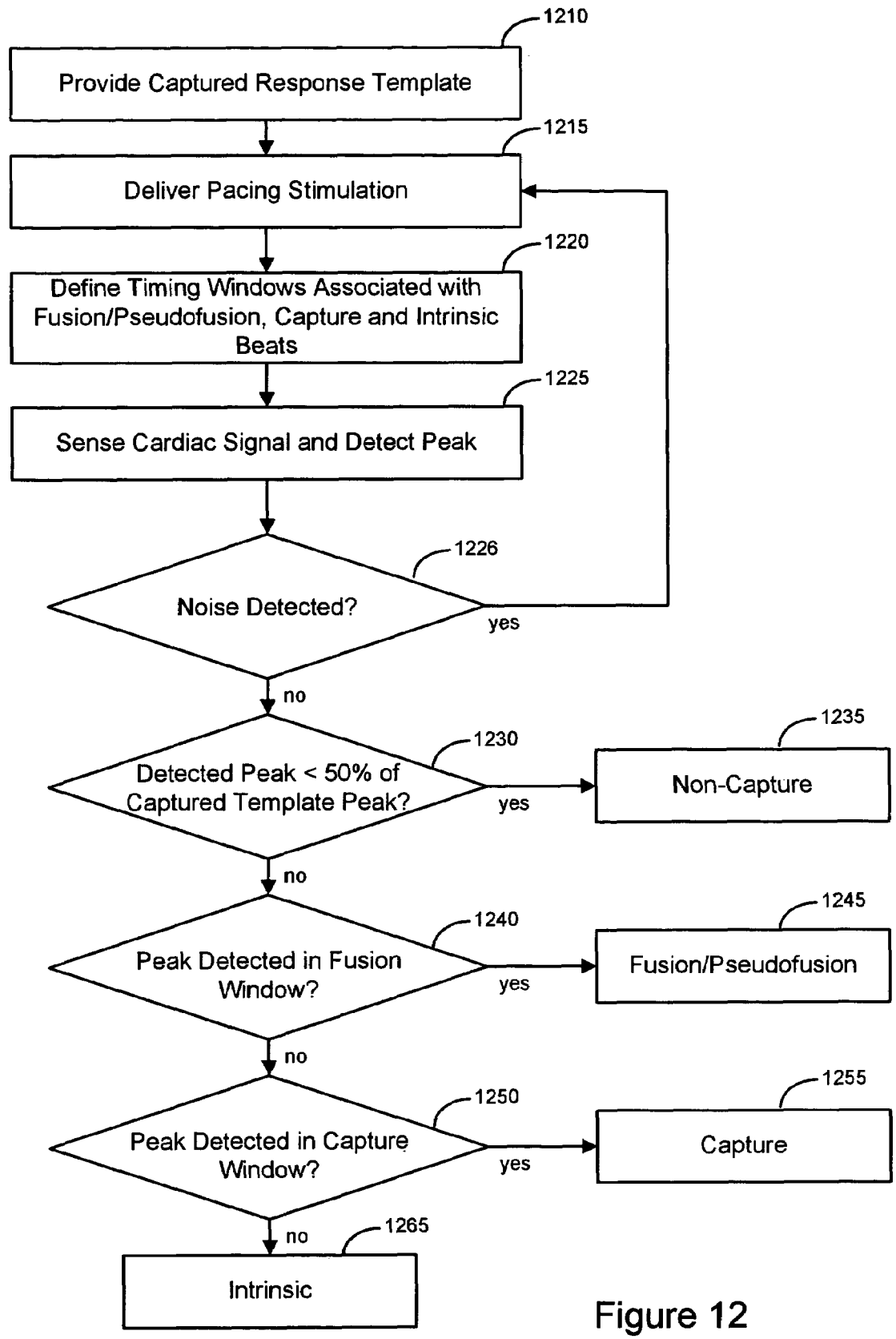
FIG. 12 is a flowchart illustrating a method of classifying a cardiac response using fusion, capture, and intrinsic classification windows in accordance with an embodiment of the invention.

The flowchart of FIG. 12 illustrates a method of classifying a cardiac response using the classification windows described in FIG. 11. A CR template is generated 1210 and the timing of the peak of the CR template is determined. A pacing stimulation is delivered 1215. Classification windows, including a fusion/pseudofusion window, a captured response window and a non-captured response window, are established 1220 based on the timing of the CR template peak relative to the pacing stimulation. The peak of a cardiac signal sensed following the pacing stimulation is detected 1225 in one of the classification windows.

If the cardiac signal is determined to be noisy 1226, then cardiac response classification is not performed for the pacing stimulation and the process continues. Commonly owned U.S. Pat. No. 6,505,071, which is incorporated herein by reference, describes methods and systems that may be utilized for noise detection in the context of the cardiac response classification processes in accordance with embodiments of the invention. If noise is not detected 1226 and if the amplitude of the detected peak is less than 1230 a reference value, then the cardiac response is classified 1235 as a non-captured response. In one embodiment, reference values used in connection with cardiac response classification may be dynamic references that are adjusted based on respiration, activity level, and lead maturation, among other factors as described in commonly owned U.S. Pat. No. 6,192,275 which is incorporated herein by reference. In another embodiment, the reference value may be a predetermined percentage, e.g., 50% of the captured response template peak. The cardiac response may be classified as a non-captured response if the cardiac signal exhibits a peak that is less than 50% of the captured response template peak, where the cardiac signal peak and the CR template peak have the same sign.

If the peak of the sensed cardiac signal is detected 1240 in the fusion/pseudofusion classification window, the cardiac response is classified 1245 as fusion or pseudofusion. If the peak of the sensed cardiac signal is detected 1250 in the captured response classification window, the cardiac response is classified 1255 as a captured response. If the peak of the cardiac signal is not detected in the fusion/pseudofusion window or the capture window, it is detected 1260 in the intrinsic classification window, and the cardiac signal is classified 1265 as an intrinsic beat.

Figure 13:
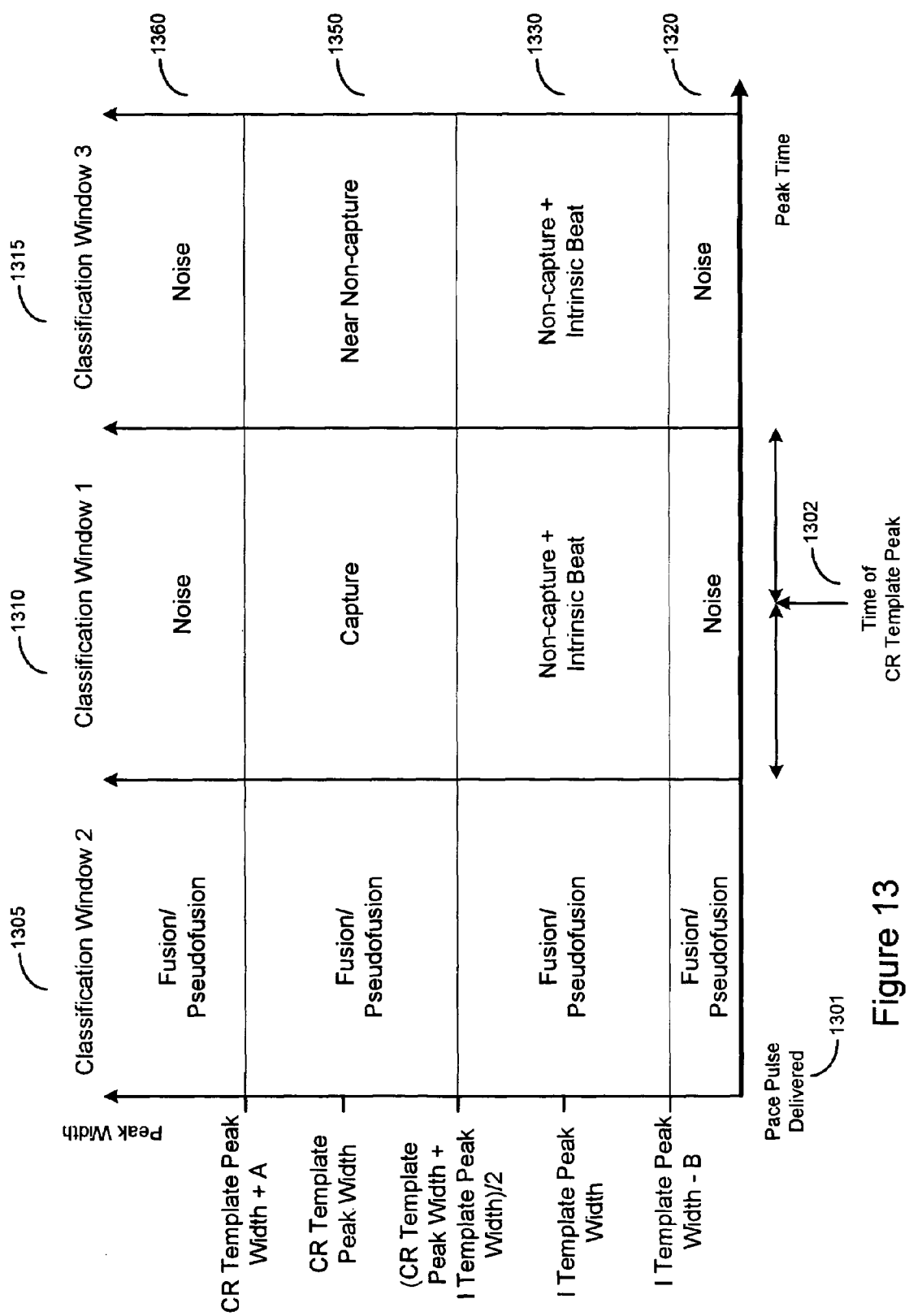
FIG. 13 is a diagram illustrating peak width classification references used to classify a cardiac response in accordance with embodiments of the invention.
Figure 14A:
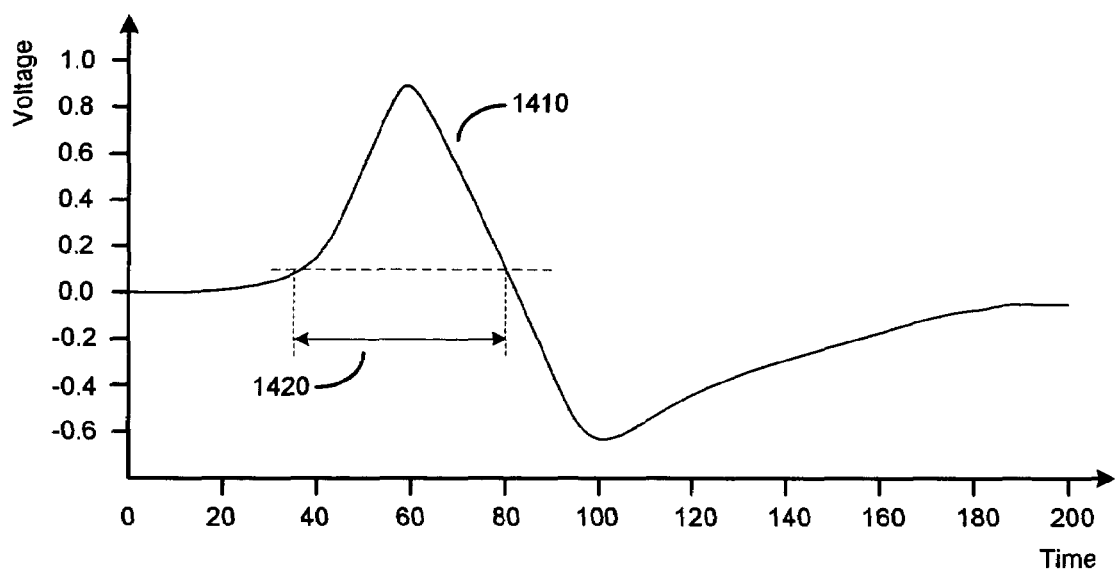
FIGS. 14A and 14B are graphs illustrating the peak width of a captured response and an intrinsic beat, respectively.
Figure 14B:
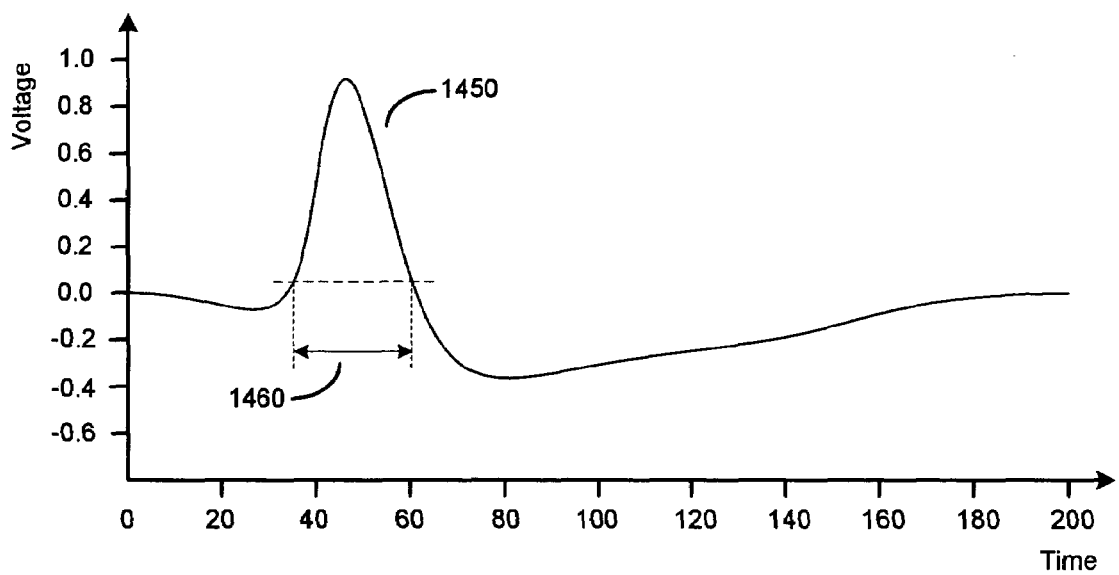
Figure 15:
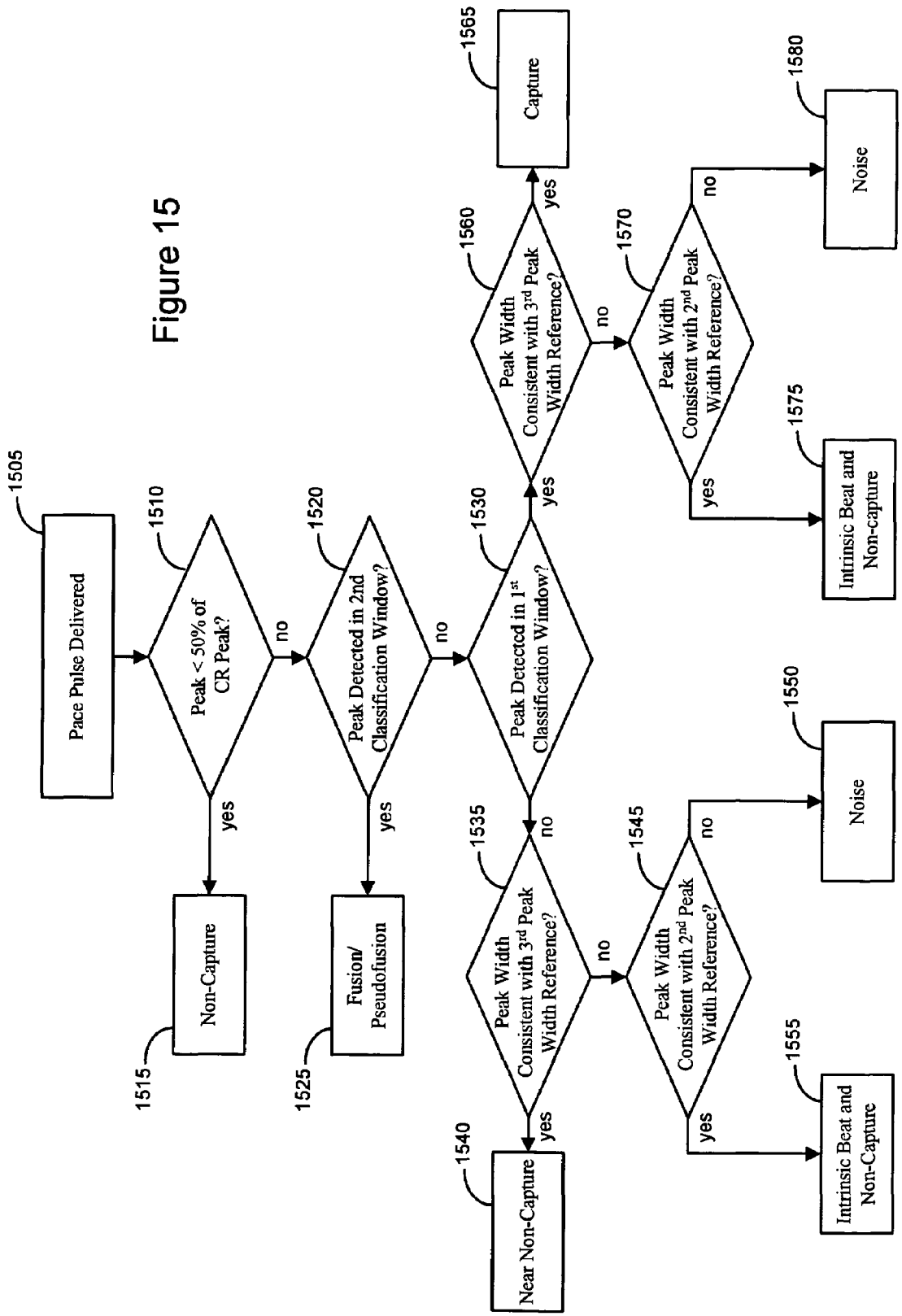
FIG. 15 is a flowchart of a method of classifying a cardiac response using peak width references according to embodiments of the invention.

FIGS. 13-15 illustrate a method of using the peak width of a cardiac signal sensed after a pacing stimulation to classify a cardiac response in accordance with embodiments of the invention. Such a method may be particularly useful, for example, in an automatic capture detection process performed on a beat-by-beat basis, but may also be used in connection with other procedures involving the classification of cardiac responses to pacing. According to the process illustrated in FIGS. 13-15, the peak width of the sensed cardiac signal is compared to one or more peak width references to determine the cardiac response. FIG. 13 illustrates the classification windows 1305, 1310, 1315 used to classify the cardiac response. The peak width of the cardiac signal may be established as a time interval that the cardiac signal remains above a predetermined percentage, e.g., 10%, or other amount, of the cardiac signal peak amplitude.

The classification windows 1305, 1310, 1315 may be established, for example, based on the time of the peak of a CR template 1302 relative to the time of the pacing stimulation 1301. In one example, a first classification window 1310 may be associated with a captured response, a second classification window 1305 may be associated with a fusion/pseudofusion response, and a third classification window 1315 may be associated with an intrinsic beat. If the peak of the sensed cardiac signal exceeds a predetermined amplitude, e.g., about 50% of the CR template peak amplitude, and is detected in one of the classification windows 1305, 1310, 1315, the peak width of the detected cardiac signal is compared to one or more peak width references. The peak width references may comprise a single peak width value, or a range of values, for example. FIG. 13 illustrates four peak width references 1320, 1330, 1350, 1360.

In this example, the each of the peak width references is associated with a range of peak widths. The peak width references are determined based on the peak width of the CR template, the peak width associated with a template characterizing an intrinsic cardiac beat (I template), or both. The CR template may be established as previously described. The peak width of the CR template may be established as the time interval that the CR template waveform remains above a predetermined percentage, e.g., 10%, or other amount, of the CR template waveform peak amplitude.

An intrinsic template (I template) characterizes the patient's supraventricular conducted rhythm (SVR). The I template may be formed from a combination of one or more beats, wherein the each beat represents the patient's SVR rhythm. The peak width of the I template may be determined, for example, as an average of the peak widths of the one or more beats used to form the I template. The peak width of each of the one or more beats used to form the I template may be established as the time interval that the beat waveform remains above a predetermined percentage, e.g., 10%, or other amount, of the peak amplitude. Specific embodiments involving I template formation are described in more detail below with reference to FIGS. 19-24.

FIGS. 14A and 14B illustrate the peak widths of cardiac signals representative of a captured response 1410 and an intrinsic beat 1450, respectively. The peak width of the captured response 1420 may be established, for example, as the time period that the cardiac signal remains above a predetermined percentage, for example, 10% or other amount, of the captured response peak. Similarly, the peak width of the intrinsic beat 1460 may be established as the time period that the cardiac signal remains above a predetermined percentage of the intrinsic beat peak.

FIG. 13 illustrates a first peak width reference 1320 comprising the range of peak widths less than or equal to the I template peak width minus B, a first predetermined amount, e.g., 10 ms or other value. A second peak width reference 1330 comprises a range of peak widths greater than the I template peak width minus B and less than or equal to an average of the CR template and I template peak widths. A third peak width reference 1350 may be established as the range of peak widths exceeding the average of the CR template and I template peak widths and less than or equal to the CR template peak width plus A, a second predetermined amount, e.g., 10 ms or other value. A fourth peak width reference 1360 may be established as the range of peak widths exceeding the CR template peak width plus A. The values of A and B may be determined based on the morphologies of the CR template and/or the intrinsic template, for example. In one implementation, the values of A and/or B may be determined based on the peak widths of the CR template and/or the intrinsic template. Further, the values of A and/or B may be adapted to track slow changes in the CR template and/or intrinsic template morphology.

The values of A and/or B may be set adaptively in response to the statistics of the variability of the peak widths over sample sets of captured and intrinsic beats. For example, A and B may be set to include a predetermined number of standard deviations of the peak width, e.g., 3 standard deviations.

The flowchart of FIG. 15 illustrates a method of classifying a cardiac response to a pacing stimulation in accordance with embodiments of the invention. The processes of FIG. 15 use the classification windows and peak width references established as illustrated in the graph of FIG. 13.

A pacing stimulation is delivered 1505 to the heart and a cardiac signal following the pacing stimulation is sensed. The amplitude and width of the cardiac signal peak are determined. If the cardiac signal peak has insufficient amplitude 1510, e.g., less than 50% of the CR template peak, then the cardiac response is classified 1515 as a non-captured response. If the cardiac signal peak has an amplitude greater than or equal to 50% of the CR template peak and the cardiac signal peak is detected 1520 in the second classification window, then the cardiac response is classified 1525 as a fusion/pseudofusion response.

If the cardiac signal peak is detected 1530 in the first classification window, then the peak width of the cardiac signal is compared to one or more peak width references to classify the cardiac response. If the peak width (PW) of the cardiac signal falls 1560 within the range of the third peak width reference, (CR template peak width+I template peak width)/2≦PW<CR template peak width+A, then the cardiac response is classified 1565 as a captured response. If the peak width (PW) of the cardiac signal falls 1570 within the range of with the second peak width reference, I template peak width−B≦PW< (CR template peak width+I template peak width)/2, then the cardiac response is classified 1575 as non-captured and intrinsic. If the peak width of the cardiac signal does not fall 1570 within the range of either the second or third peak width references, then it falls into the ranges of the first peak width reference, PW≦CR template peak width A, or the fourth peak width reference, PW<I template peak width−B, and is classified 1580 as noise.

If the cardiac signal peak is not detected 1520 in the second classification window and is also not detected 1530 in the first classification window, then it falls within the third classification window. The cardiac signal peak width is compared to one or more peak width references to determine the cardiac response. If the peak width falls 1535 within the range of the third peak width reference, the cardiac response is classified 1540 as near non-capture. A near non-captured response comprises a response that occurs when the pacing stimulation is captured but delayed.

If the peak width of the cardiac signal falls 1545 within the range of the second peak width reference, then the cardiac response is classified 1555 as a non-captured response plus an intrinsic beat. If the peak width of the cardiac signal does not fall 1545 within the range of either the second peak width reference or the third peak width reference, then the peak width falls into either the range of the first peak width reference or the fourth peak width reference and is classified 1550 as noise.

The cardiac response classification methods of the invention as described below may be particularly useful in an automatic capture threshold determination procedure. A capture threshold test may initially deliver pacing at a high energy level, thus ensuring captured responses. The pacing energy level may be ramped down from the initial high energy level until loss of capture is detected. The point just before loss of capture occurs may be established as the capture threshold.

Figure 16:
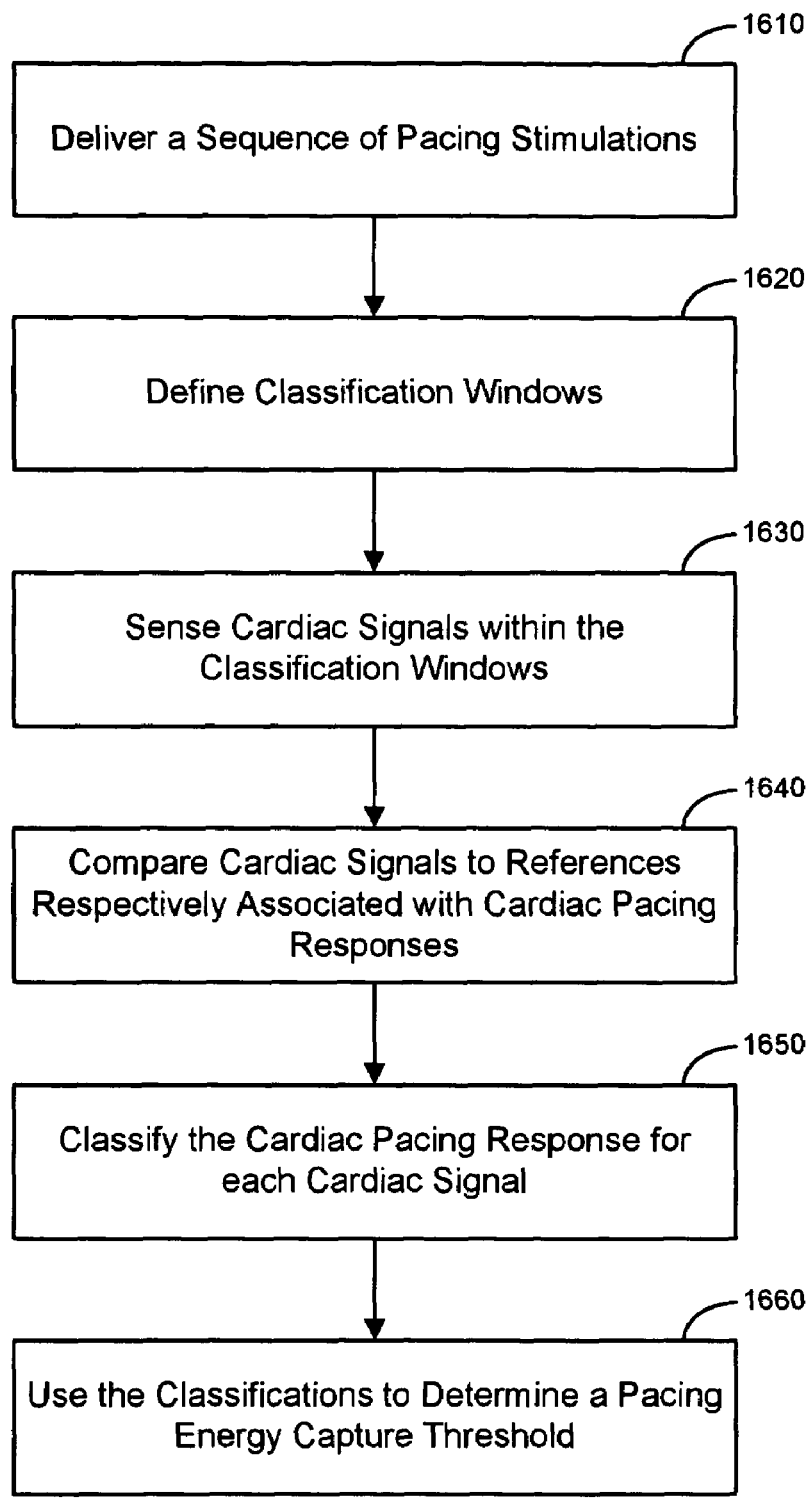
FIG. 16 is a flowchart of a method of implementing a cardiac response classification process in accordance with the embodiments of the invention.

The flowchart of FIG. 16 illustrates a process that is particularly useful for performing a capture threshold determination process based on cardiac response classification in accordance with embodiments of the invention. Although this process is described in terms of a capture threshold procedure, the methods of cardiac response classification may be used in connection with other procedures including, for example, beat by beat automatic capture verification.

A sequence of pacing pulses are delivered 1610 to the heart. For example, the pacing pulses may have an initially high energy level with the pacing energy level decreasing in discrete steps. For each delivered pace pulse, a plurality of classification windows are established 1620 relative to and following the time of each pace pulse. Cardiac signals following the pacing pulses are sensed 1630 within the classification windows. The cardiac signals are compared 1640 to references respectively associated with different types of cardiac responses. The cardiac response to each of the pace pulses is classified 1650 based on the comparisons. The classifications of the cardiac responses are used 1660 to determine a pacing energy capture threshold.

In one example, the pacing energy of the pacing pulses is ramped down from an initially high pacing energy. The cardiac response following the delivery of each pacing pulse is determined as described in connection with the flowchart of FIG. 16. When a predetermined number of pacing pulses produce a non-captured response, e.g., about two out of three delivered pacing pulses, loss of capture is determined. The point just before loss of capture occurs comprises the capture threshold.

Figure 17:
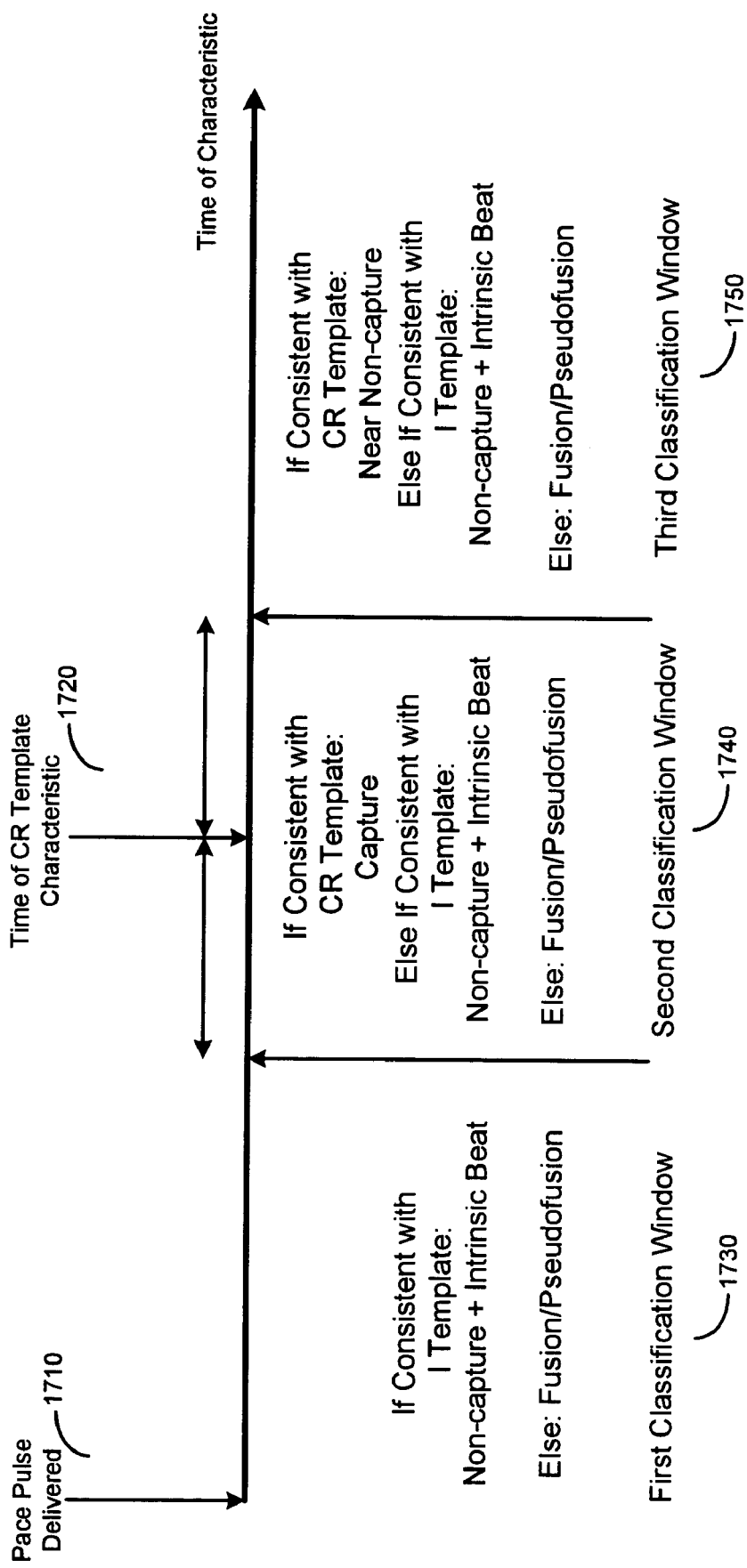
FIG. 17 is a diagram illustrating the use of captured response and intrinsic beat templates in connection with classification of a cardiac response in accordance with embodiments of the invention.

FIG. 17 is a diagram illustrating classification windows and references that may be used in determining a cardiac pacing response according to embodiments of the invention. In this example embodiment, first, second, and third classification windows 1730, 1740, 1750 are established based on the timing of a particular CR template characteristic 1720, such as the peak of the CR template, relative to the time of the delivery of the pace pulse 1710. A selected characteristic of the cardiac signal following the pace pulse, e.g., the peak of the cardiac signal, is detected in one of the classification windows 1730, 1740, 1750. Depending upon the particular classification window in which the selected characteristic is detected, features of the cardiac signal are compared to one or more references. The references may include, for example, templates characterizing various types of cardiac responses, including the CR template and/or the I template. The cardiac response is classified based on the comparison of the cardiac signal feature or features and the one or more references, and the particular window in which the selected characteristic of the cardiac signal is detected.

Figure 18:
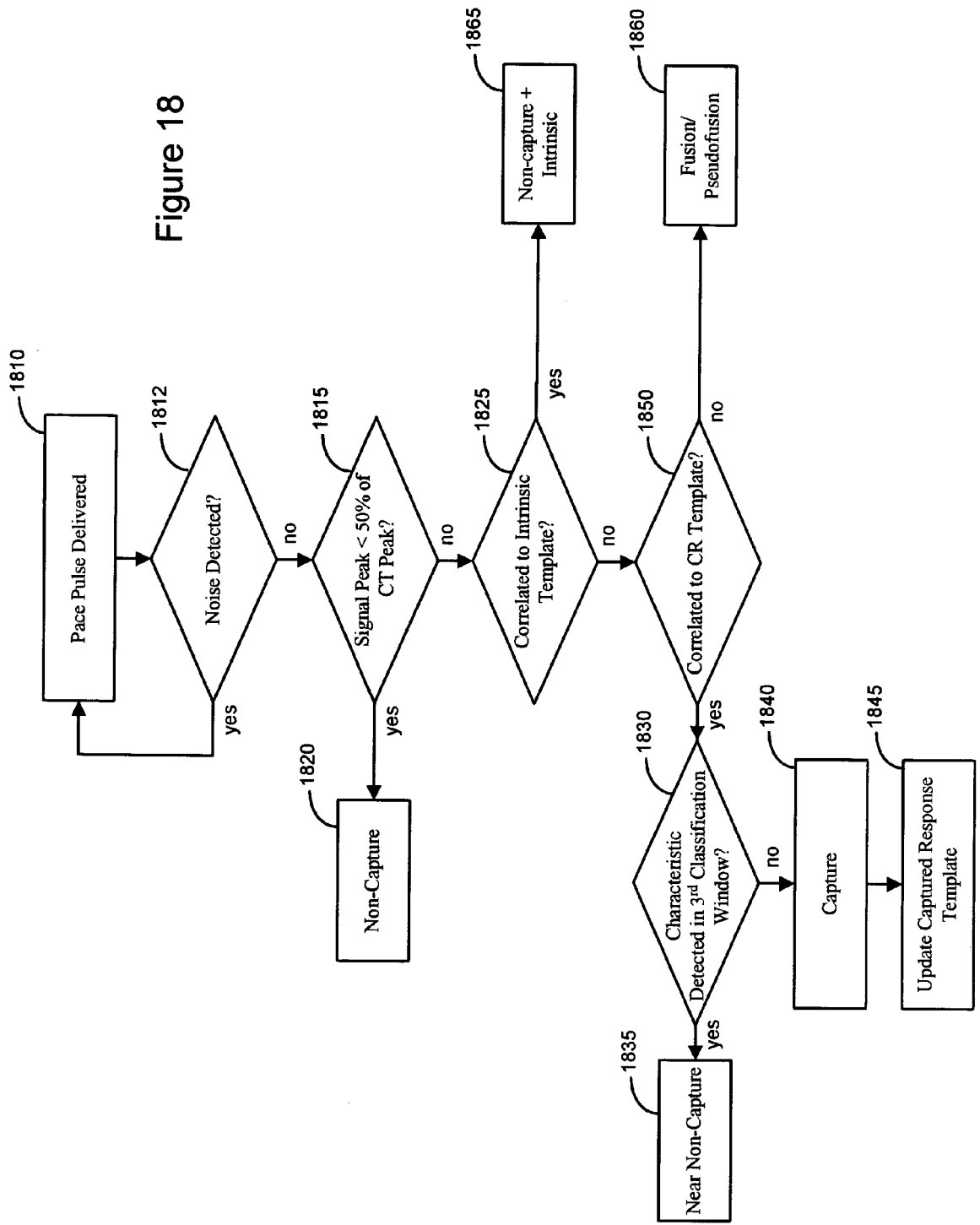
FIG. 18 is a flowchart of a method of using template references to classify a cardiac response in accordance with embodiments of the invention.

The flowchart of FIG. 18 provides a more detailed illustration of a method of classifying a cardiac response following a pacing pulse based on a comparison between the cardiac signal and the CR template or the I template, for example. The method described with reference to FIGS. 17 and 18 make use of cardiac signal morphology templates including the captured response (CR) template and the intrinsic response I template. The method described in connection with FIG. 18 may be particularly useful in connection with an automatic capture threshold detection procedure.

As discussed previously, a captured response (CR) template exemplifies a waveform representative of a captured response. The CR template may be derived from a waveform that is produced when a pacing pulse captures the heart, and includes both the evoked response and the superimposed pacing artifact. A CR template may comprise, for example, a sequence of samples or feature points of a cardiac signal representing a captured response.

An intrinsic response template, referred to herein as an I template, characterizes the morphology of an electrical signal associated with the patient's intrinsic or supraventricular conducted cardiac rhythm (SVR). Processes for forming templates representing the patient's supraventricular conducted rhythm (SVR) using a two channel procedure are described in commonly owned U.S. Pat. Nos. 6,708,058;

7,184,818; 7,085,599; 6,889,079; and 6,449,503 all of which are incorporated herein by reference.

An I template may be formed from a combination of one or more beats, wherein each beat represents the patient's intrinsic or SVR rhythm. Cardiac beats used to form the I template may be required to meet certain criteria, such as stability and/or rate criteria. According to one embodiment, an I template generation process involves sensing cardiac signals on a rate channel and on a shock channel. Shock channel automatic gain control may be performed prior to collecting beats for I template generation. For example, the shock channel gain control may be effected by measuring the peak value in four beats meeting certain rate and stability criteria and adjusting the shock channel gain such that the averaged peak value is 50% of the maximum A/D converter value.

According to a two channel approach for template generation, a peak of the rate channel signal is determined and identified as the fiducial point. The value and location of features of the initial shock channel waveform are determined relative to the rate channel fiducial point. Additional cardiac signals, including rate channel signals and shock channel signals are sensed. The fiducial points for the additional rate channel signals are determined. The shock channel waveforms are then aligned with the I template using the fiducial points developed from the rate channel signals. The I template is generated using features extracted from the aligned shock channel waveforms.

Figure 19:
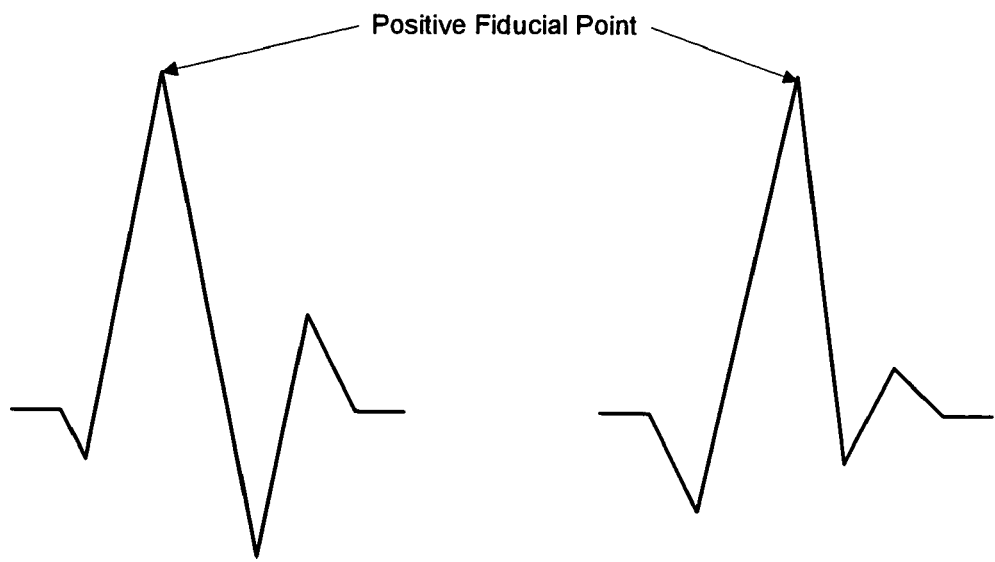
FIGS. 19 and 20 illustrate positive and negative type fiducial points determined from rate channel signals in accordance with embodiments of the invention.
Figure 20:
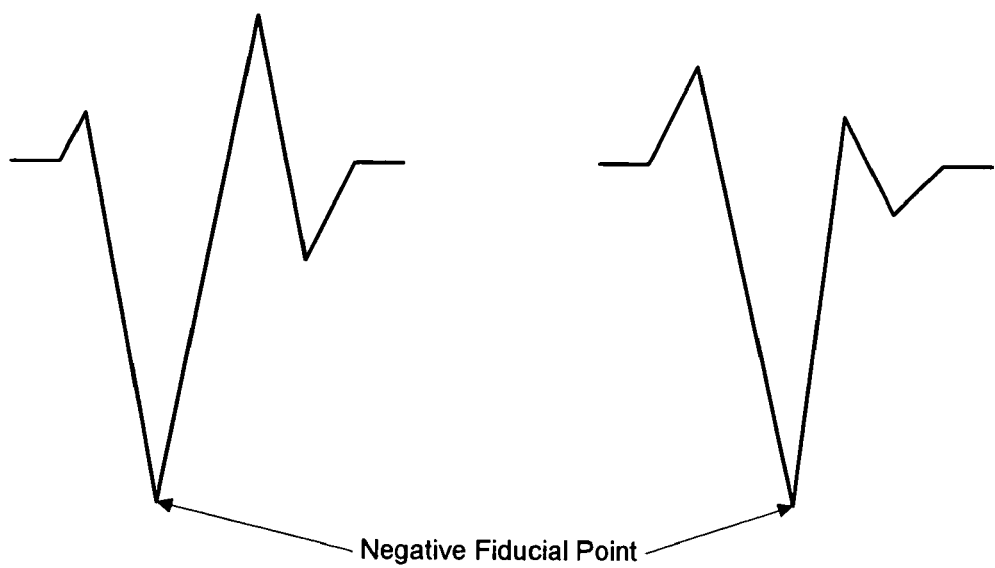

A fiducial point represents a peak value of the rate channel signal. A fiducial point type is either positive (Pos), associated with a positive peak, or negative (Neg), associated with a negative peak. When a template is formed, the positive peak (Pos) or the negative peak (Neg) of the rate channel signal used to form the template determines the fiducial point type of the template. FIGS. 19 and 20 depict positive and negative fiducial points, respectively. The Pos and Neg peaks are measured as absolute values. The fiducial point type is determined by Equation 3 as follows:

If Pos>0.9*Neg, the fiducial point type is positive

If Pos≦0.9*Neg, the fiducial point type is negative  [3]

If a stored I template exists, the fiducial point type of the stored template is used as the fiducial point type of the template. If no stored template exists, the fiducial point type of the first beat used to form the template is used as the fiducial point type for the template.

Figure 21:
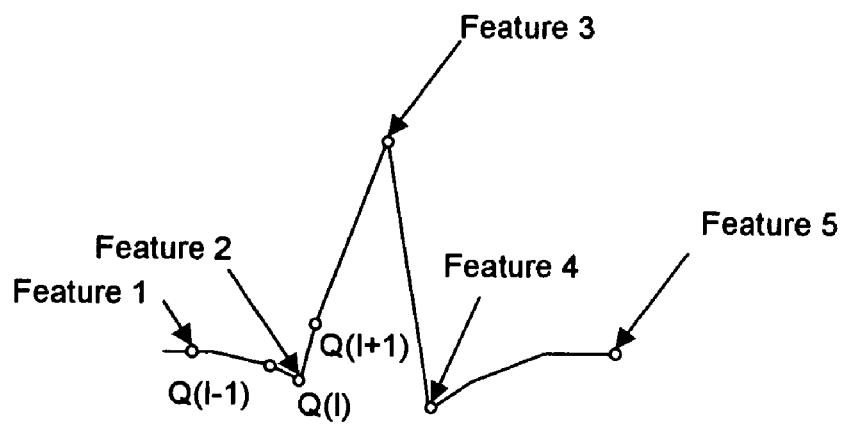
FIGS. 21 and 22 show morphological features, including turning point and flat slope features, respectively, for choosing template features in accordance with embodiments of the invention.
Figure 22:
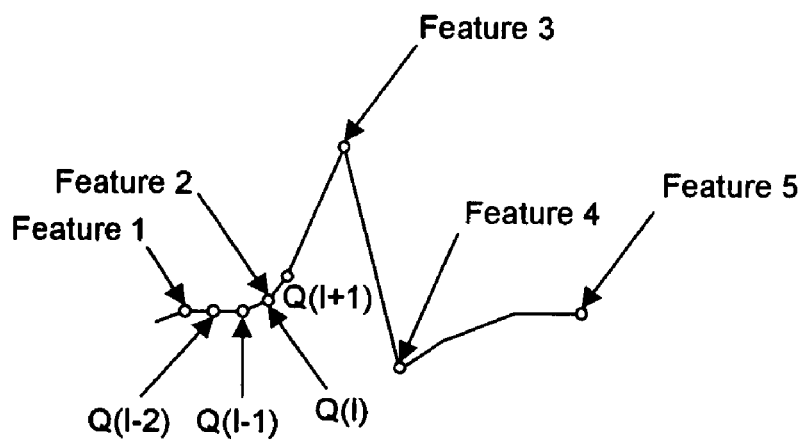

In one embodiment of the invention, and with reference to FIGS. 21 and 22, five features are initially identified for the I template, followed by three additional features determined at midpoints between certain ones of the five initially selected features.

Feature 3 is selected as the absolute maximum peak in a feature window defined by 31 samples centered at the fiducial point. If the positive peak amplitude is equal to the negative peak amplitude, the positive peak is selected as Feature 3.

Feature 2 is found by searching backward from Feature 3 until a point is reached that meets the following conditions: 1) the search is limited to 10 samples. If no point satisfies the following conditions, then the 10th sample becomes Feature 2; 2) the amplitude is less than 25% of the maximum peak; 3) a turning point is found or the slope is flat, and 4) Feature 2 is at least 4 samples away from Feature 3.

By way of example, let Q(I) represent the current sample. A turning point is found if:

$Q(I-1) \geq Q(I)$ and $Q(I) < Q(I+1)$ for a positive Feature 3

$Q(I-1) \geq Q(I)$ and $Q(I) > Q(I+1)$ for a negative Feature 3  [4]

As is shown in FIG. 21, Q(I) is selected as Feature 2. As such, Feature 2 is selected as a turning point.

The slope is considered flat, as shown in FIG. 22, if abs(Q(I+1)−Q(I−1))<4 and abs(Q(I+1)−Q(I−2))<4, in the case when the A/D converter maximum value is 128. In the illustrative depiction of FIG. 22, Q(I) is selected as Feature 2. As such, Feature 2 is selected as a flat slope point.

Feature 4 is found by searching forward starting from Feature 3 until a point is reached that meets the following conditions: 1) the search is limited to 16 samples. If no point satisfies the following conditions, then the 16th sample becomes Feature 4; 2) the amplitude is less than 25% of the maximum peak; and 3) a turning point is found or the slope is flat.

By way of example, let Q(I) represent the current sample. A turning point is found if:

$Q(I+1) \geq Q(I)$ and $Q(I) < Q(I-1)$ for a positive Feature 3

$Q(I+1) \leq Q(I)$ and $Q(I) > Q(I-1)$ for a negative Feature 3  [5]

Figure 23:
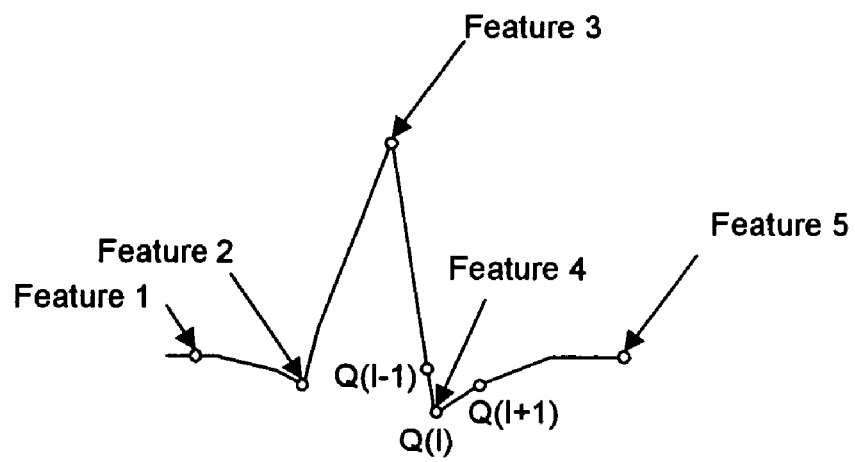
FIGS. 23 and 24 show morphological features, including turning point and flat slope features, respectively, for choosing template features in accordance with embodiments of the present invention.

Q(I) is selected as Feature 4, as is shown in FIG. 23.

Figure 24:
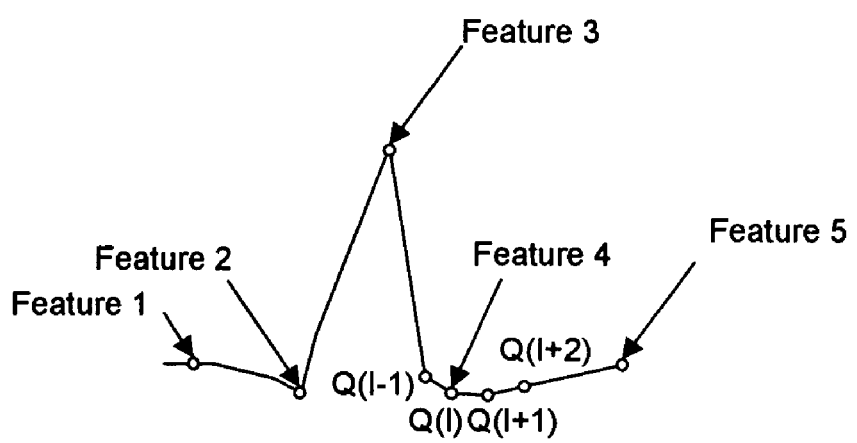

The slope is flat, as shown in FIG. 24, if abs(Q(I−1)−Q(I+1))<4 and abs(Q(I−1)−Q(I+2))<4. In this case, Q(I) is selected as Feature 4.

Feature 1 is selected as the seventeenth sample from the beginning of the detection window. Feature 5 is selected as the last sample of the detection window. Three additional features are selected at the midpoint of Features 1 and 2, the midpoint of Features 2 and 3, and the midpoint of Features 3 and 4, respectively. If a midpoint falls between two sample points, the leftmost (earlier in time) point is selected. Thus, according to this embodiment, eight feature values (e.g., amplitudes) and their associated locations with respect to the fiducial point and the corresponding fiducial point type are saved as the I template.

Following generation of an I template, a subsequently detected cardiac beat may be compared to the I template to classify the cardiac beat. If the cardiac beat has a morphology similar to that of an intrinsic beat, then the features of the cardiac beat will be correlated to the template features. Various steps associated with determining if a cardiac beat is correlated to an I template in accordance with embodiments of the invention are described below.

The rate channel signal and the shock channel signal for the cardiac beat are sensed. The fiducial point of the rate channel signal is determined. The rate channel fiducial point is used to align the rate and shock channel waveforms of the cardiac beat with the template. Features of the shock channel signal are determined at the locations relative to the fiducial point previously determined for the template. The template features and the cardiac signal features are compared by calculating a feature correlation coefficient (FCC). In one particular embodiment, Equation 6, provided below, is used to compute the FCC between the template features and the cardiac signal features.

$$FCC = \frac{\left(N\sum_{i=1}^{N} X_i Y_i - \left(\sum_{i=1}^{N} X_i\right)\left(\sum_{i=1}^{N} Y_i\right)\right)^2}{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)} \quad [6]$$

where, Xi represents template N features and Yi represents beat N features, and N=8 in this illustrative example. The sign of the numerator term is checked before squaring. If the numerator is negative, the beat is uncorrelated, and the remainder of the computation need not be performed.

If the FCC is greater than a predetermined value, for example 0.94, then the cardiac beat is correlated to the template. If the FCC is less than or equal to the predetermined value, then the cardiac beat is uncorrelated to the template.

Alternatively, correlation between the cardiac beat and the template may be calculated using the CWA technique described by Equation 1 above. Other techniques may also be implemented to generate templates and to compare templates and the cardiac signals.

For example, an alternate methodology for generating templates representative of various types of cardiac signals is described in commonly owned U.S. Pat No. 6,684,100, which is incorporated herein by reference. The application cited immediately above describes a curvature-based method for selecting features of a template, e.g., an I template for example. The curvature-based method of template formation may be used in the cardiac response classification processes described herein.

The flowchart of FIG. 18 illustrates a method for classifying a cardiac signal following deliver of a pacing pulse based on comparison of the cardiac signal one or more of a CR template and an I template. Following the delivery 1810 of a pace pulse to the heart, classification windows such as those described in connection with FIG. 17 are established relative to the timing of the pace pulse. The peak of the cardiac signal following the pace pulse is detected in one of the established classification windows. The peak amplitude of the cardiac signal is determined.

If noise is detected 1812, then cardiac response classification is not performed for the pacing stimulation and the process continues. If noise is not detected 1812 and if the peak amplitude of the cardiac signal is less than 1815 a predetermined value, for example, about 50% of the CR template peak amplitude, then the cardiac response is classified as a non-captured response. If the peak amplitude of the cardiac signal is greater than or equal to 1815 the predetermined value, then the cardiac signal may be compared to one or more references to classify the cardiac response to the pacing stimulation.

If the cardiac signal peak amplitude is greater than or equal to 1815 the predetermined value, then cardiac signal is compared to the intrinsic template. If the cardiac signal is correlated 1825 to the I template then the cardiac response is classified 1865 as a non-captured response and intrinsic beat. Correlation may be determined by calculating a feature correlation coefficient representing the degree of correlation between the cardiac signal and the I template using Equation 5 above. For the purposes of cardiac response classification, a cardiac signal is determined to be correlated to the intrinsic beat template if the FCC is about 0.94.

If the cardiac signal is not correlated 1825 to the I template, then correlation with the CR template is checked 1850. The comparison of the cardiac signal to the CR template may be performed, for example, by calculating a correlation coefficient (CC) representing the degree of correlation between the cardiac signal and the captured response template using a technique such as Correlation Waveform Analysis (CWA). In one particular embodiment, Equation 1, provided above, is used to compute the CC between the samples of a cardiac signal and the captured response template samples. Typically, the number of samples used for the calculation is about 33 samples. If the correlation coefficient is greater than a predetermined value, for example, about 0.94, the cardiac signal is considered to be correlated to the CR template. If the cardiac signal is not correlated 1850 to the CR template, then the cardiac response is classified 1860 as a fusion/pseudofusion response.

If the cardiac signal is correlated 1850 to the CR template and the peak of the cardiac signal is detected 1830 within the third classification window, illustrated in FIG. 17, then the cardiac response is determined 1835 to be near non capture. If the peak of the cardiac signal is not detected 1830 in the third classification window, then the cardiac response is classified 1840 as capture and the CR template may be updated 1845 using the cardiac signal.

Although the examples illustrated in FIGS. 11-18 are described in terms of using a CR template for cardiac response classification, similar approaches may be implemented using an ER template. In processes using an ER template, the pacing artifact template may be subtracted or otherwise cancelled from the sensed cardiac signal prior to analyzing the sensed cardiac signal to determine the cardiac response.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of classifying a cardiac response to a pacing pulse, comprising:
   defining a plurality of classification windows relative to and subsequent to the pacing pulse wherein the plurality of windows comprise, a first classification window predominantly associated with a captured response, a second classification window predominantly associated with a fusion/pseudofusion response, and a third classification window predominantly associated with a non-captured response;
   sensing a cardiac signal following the pacing pulse;
   detecting one or more characteristics of the cardiac signal within one or more particular classification windows of the plurality of classification windows; and
   classifying the cardiac response to the pacing pulse based on the one or more detected characteristics and the one or more particular classification windows.

2. The method of claim 1, further comprising:
   detecting noise on the cardiac signal; and
   canceling the classification of the cardiac response based on the detection of noise.

3. The method of claim 1, wherein defining the plurality of classification windows comprises defining a plurality of non-overlapping classification windows.

4. The method of claim 1, wherein defining the plurality of classification windows comprises adapting a timing of a particular classification window.

5. The method of claim 1, wherein defining the plurality of classification windows comprises adapting a duration of a particular classification window.

6. The method of claim 1, wherein defining the plurality of classification windows comprises:
defining a first classification window based on a timing of a cardiac signal feature associated with a captured response; and
defining one or more additional classification windows in relation to the first classification window.

7. The method of claim 6, wherein defining the first classification window based on the timing of the feature associated with the captured response comprises defining the first classification window based on the timing of a captured response template peak.

8. The method of claim 6, wherein defining the first classification window based on the timing of the feature associated with the captured response comprises defining the first classification window based on the timing of an evoked response template peak.

9. The method of claim 6, wherein defining the one or more additional classification windows comprises:
defining a second classification window to occur before the first classification window; and
defining a third classification window to occur after the first classification window.

10. The method of claim 1, wherein detecting the one or more characteristics of the cardiac signal comprises detecting one or more morphological features of the cardiac signal.

11. The method of claim 1, wherein detecting the one or more characteristics of the cardiac signal comprises detecting a peak of the cardiac signal.

12. The method of claim 1, wherein detecting the one or more characteristics of the cardiac signal comprises detecting a peak width of the cardiac signal.

13. The method of claim 1, wherein classifying the cardiac response comprises comparing the one or more characteristics to one or more references respectively associated with one or more types of cardiac responses.

14. The method of claim 13, wherein the one or more references are adaptable.

15. The method of claim 13, wherein a particular reference is adaptable based on a statistical variability of the particular reference.

16. The method of claim 1, wherein classifying the cardiac response comprises classifying the cardiac response as a captured response.

17. The method of claim 1, wherein classifying the cardiac response comprises classifying the cardiac response as a non-captured response.

18. The method of claim 1, wherein classifying the cardiac response comprises classifying the cardiac response as a non-captured response and an intrinsic beat.

19. The method of claim 1, wherein classifying the cardiac response comprises classifying the cardiac response as a near non-captured response.

20. The method of claim 1, wherein classifying the cardiac response comprises classifying the cardiac response as a fusion/pseudofusion beat.

21. The method of claim 1, wherein:
detecting the one or more characteristics of the cardiac signal comprises detecting an amplitude of the cardiac signal; and
classifying the cardiac response comprises:
comparing the detected amplitude to an amplitude reference; and
classifying the cardiac response based on the comparison.

22. The method of claim 1, wherein:
detecting the one or more characteristics of the cardiac signal comprises detecting a slope of the cardiac signal; and
classifying the cardiac response comprises:
comparing the detected slope to a slope reference; and
classifying the cardiac response based on the comparison.

23. The method of claim 1, wherein:
detecting the one or more characteristics of the cardiac signal comprises detecting a curvature of the cardiac signal; and
classifying the cardiac response comprises:
comparing the detected curvature to a curvature reference; and
classifying the cardiac response based on the comparison.

24. The method of claim 1, wherein:
detecting the one or more characteristics of the cardiac signal comprises detecting a peak width of the cardiac signal; and
classifying the cardiac response comprises:
comparing the detected peak width to a peak width reference; and
classifying the cardiac response based on the comparison.

25. The method of claim 1, wherein:
detecting the one or more characteristics of the cardiac signal comprises detecting one or more feature points of the cardiac signal; and
classifying the cardiac response comprises:
providing a template;
comparing the one or more feature points to the template; and
classifying the cardiac response based on the comparison.

26. The method of claim 25, wherein providing the template comprises providing a captured response template.

27. The method of claim 26, wherein providing the captured response template comprises updating the captured response template using one or more additional captured response beats.

28. The method of claim 26, wherein providing the captured response template comprises forming the captured response template using one or more captured response beats.

29. The method of claim 26, wherein forming the captured response template comprises:
delivering one or more pacing pulses at a energy level exceeding a capture threshold;
sensing one or more cardiac signals following the pacing pulses; and
forming the captured response template using the one or more cardiac signals.

30. The method of claim 29, wherein delivering the one or more pacing pulses at an energy level exceeding the capture threshold comprises delivering the one or more pacing pulses during a capture threshold test.

31. The method of claim 25, wherein providing the template comprises providing an intrinsic beat template.

32. The method of claim 31, wherein providing the intrinsic beat template comprises forming the intrinsic template using one or more cardiac beats representative of an intrinsic cardiac beat.

33. The method of claim 32, wherein forming the intrinsic beat template using one or more beats representative of an intrinsic cardiac beat comprises:
   sensing rate channel signals of the one or more cardiac beats;
   sensing shock channel signals of the one or more cardiac beats; and
   forming the intrinsic template using the rate channel signals and the shock channel signals.

34. The method of claim 25, wherein providing the template comprises providing an evoked response template.

35. The method of claim 34, wherein providing the evoked response template comprises:
   providing a captured response template;
   canceling a pacing artifact from the captured response template; and
   forming the evoked response template using the pacing artifact canceled captured response template.

36. A method of classifying cardiac pacing responses, comprising:
   defining a plurality of classification windows relative and subsequent to each pacing stimulation;
   sensing cardiac signals following the pacing stimulations;
   detecting characteristics of the cardiac signals within particular classification windows,
   comparing one or more characteristics of a cardiac signal to a captured response template and an intrinsic response template; and
   classifying a cardiac pacing response as a fusion/pseudofusion beat if the one or more characteristics are not consistent with the captured response template or the intrinsic response template.

37. The method of claim 36, further comprising:
   detecting noise on the cardiac signals; and
   canceling classification of the cardiac pacing responses based on the detection of noise.

38. The method of claim 36, further comprising using the classifications of the cardiac pacing responses to determine a pacing energy capture threshold.

39. The method of claim 38, wherein;
   delivering the sequence of pacing stimulations to a heart comprises delivering a sequence of pacing stimulations of variable energy; and
   using the classifications to determine the pacing energy capture threshold comprises:
      detecting loss of capture if a predetermined number of cardiac pacing responses are classified as non-captured responses; and
      determining the pacing energy capture threshold based on the loss of capture detection.

40. The method of claim 39, wherein detecting loss of capture comprises detecting loss of capture if a predetermined number of cardiac responses are classified as non-captured responses.

41. The method of claim 40, wherein the predetermined number of cardiac responses is about two out of about three cardiac responses.

42. The method of claim 41, further comprising generating a captured response template using one or more cardiac signals associated with captured responses.

43. The method of claim 39, wherein delivering the sequence of pacing stimulations comprises delivering a sequence of pacing stimulations of decreasing energy.

44. The method of claim 39, wherein delivering the sequence of pacing stimulations comprises delivering a sequence of pacing stimulations of increasing energy.

45. The method of claim 36, wherein classifying the cardiac pacing responses comprises classifying a non-captured response.

46. The method of claim 36, wherein classifying the cardiac pacing responses comprises classifying a captured response.

47. The method of claim 36, wherein classifying the cardiac pacing responses comprises classifying a fusion/Pseudofusion response.

48. The method of claim 36, wherein classifying the cardiac pacing responses comprises classifying a near non-captured response.

49. The method of claim 36, wherein classifying the cardiac pacing responses comprises classifying a non-captured response and an intrinsic beat.

50. The method of claim 36, wherein:
   comparing the characteristics to the one or more references comprises comparing a peak amplitude of a particular cardiac signal to a peak amplitude reference; and
   classifying the cardiac pacing responses comprises classifying a particular cardiac response as a non-captured response if the particular cardiac signal has a peak amplitude less than the peak amplitude reference.

51. The method of claim 36, wherein:
   detecting the characteristics within the particular classification windows comprises detecting one or more characteristics of a particular cardiac signal within a particular classification window associated with a peak time of a captured response template;
   comparing the characteristics to the one or more references comprises comparing the one or more characteristics to the captured response template; and
   classifying the cardiac pacing responses comprises classifying a particular cardiac pacing response as a captured response if the one or more characteristics are consistent with the captured response template.

52. The method of claim 36, wherein:
   detecting the characteristics within the particular classification windows comprises detecting one or more characteristics of a particular cardiac signal within a particular classification window associated with a peak time of an evoked response template;
   comparing the characteristics to the one or more references comprises comparing the one or more characteristics to the evoked response template; and
   classifying the cardiac pacing responses comprises classifying a particular cardiac pacing response as a captured response if the one or more characteristics are consistent with the evoked response template.

53. The method of claim 36, wherein:
   comparing the characteristics to the one or more references comprises comparing one or more characteristics of a particular cardiac signal to an intrinsic beat template; and
   classifying the cardiac pacing responses comprises classifying a particular cardiac pacing response as a non-captured response and an intrinsic beat if the one or more characteristics are consistent with the intrinsic beat template.

54. The method of claim 36, wherein:
   detecting characteristics of cardiac signals following the pacing stimulations comprises:
      canceling a pacing artifact from each sensed cardiac signal; and detecting one or more characteristics of each sensed cardiac signal within one or more particular classification windows;
comparing the one or more characteristics to one or more references respectively associated with types of cardiac pacing responses; and
classifying a cardiac pacing response based on the comparisons and the one or more particular classification windows.

55. A capture verification method, comprising:
delivering a pacing stimulation;
defining a plurality of classification windows relative and subsequent to the pacing stimulation wherein the plurality of windows comprise, a first classification window predominantly associated with a captured response, a second classification window predominantly associated with a fusion/pseudofusion response, and a third classification window predominantly associated with a non-captured response;
sensing a cardiac signal following the pacing stimulation;
detecting a peak of the sensed cardiac signal occurring within a particular classification window; and
determining a cardiac response based on the detected peak and the particular classification window.

56. The method of claim 55, wherein detecting the peak of the sensed cardiac signal comprises detecting a peak having an amplitude greater than a reference value.

57. The method of claim 56, wherein the reference value is about 50% of a captured response template peak.

58. The method of claim 56, wherein the reference value is adaptable.

59. The method of claim 55, wherein determining the cardiac response based on the detected peak and the particular classification window comprises classifying the cardiac response as a captured response if the detected peak has an amplitude greater than a reference value and occurs within the first classification window.

60. The method of claim 55, wherein determining the cardiac response based on the detected peak and the particular classification window comprises determining a fusion/pseudofusion response if the detected peak has an amplitude greater than a reference value and occurs within the second classification window.

61. The method of claim 55, wherein determining the cardiac response based on the detected peak and the particular classification window comprises determining an intrinsic response if the detected peak has an amplitude greater than a reference value and occurs within the third classification window.

62. The method of claim 55, wherein:
detecting the peak of the sensed cardiac signal occurring within a particular classification window comprises determining a peak width of the cardiac signal; and
determining the cardiac pacing response comprises comparing the cardiac signal peak width to one or more peak width references.

63. The method of claim 55, wherein:
detecting the peak of the sensed cardiac signal comprises determining a peak width of the cardiac signal peak; and
determining the cardiac response comprises:
comparing the cardiac signal peak width to a captured response peak width reference; and
classifying the cardiac response as a captured response if the cardiac signal peak width is consistent with the captured response peak width reference.

64. The method of claim 55, wherein:
detecting the peak of the sensed cardiac signal comprises determining the peak width of the cardiac signal peak; and
determining the cardiac response comprises:
comparing the cardiac signal peak width to a non-captured response peak width reference; and
classifying the cardiac response as a non-captured response if the cardiac signal peak width is consistent with the non-captured response peak width reference.

65. The method of claim 55, wherein:
detecting the peak of the sensed cardiac signal comprises determining the peak width of the cardiac signal peak; and
determining the cardiac response comprises:
comparing the cardiac signal peak width to a noise peak width reference; and
classifying the cardiac response as noise if the cardiac signal peak width is consistent with the noise peak width reference.

66. The method of claim 55, wherein:
detecting the peak of the sensed cardiac signal comprises determining a width of the cardiac signal peak; and
determining the cardiac response comprises;
comparing the cardiac signal peak width to a near non-captured response peak width reference; and
classifying the cardiac response as a near non-captured response if the cardiac signal peak width is consistent with the near non-captured response peak width reference.

67. The method of claim 55, wherein:
detecting the peak of the sensed cardiac signal comprises determining a peak width of the cardiac signal peak; and
determining the cardiac response comprises:
comparing the cardiac signal peak width to a non-captured response and intrinsic beat peak width reference; and
classifying the cardiac response as a non-captured response and an intrinsic beat if the cardiac signal peak width is within the non-captured response and intrinsic beat peak width reference.

68. A medical device, comprising:
a pacing pulse delivery circuit configured to deliver a pacing pulse to a heart;
a sensing circuit configured to sense a cardiac signal associated with the pacing pulse; and
a control circuit, coupled to the sensing circuit and configured to define a plurality of classification windows relative to and following the pacing pulse, wherein the plurality of windows comprise a first classification window predominantly associated with a captured response, a second classification window predominantly associated with a fusion/pseudofusion response, and a third classification window predominantly associated with a non-captured response, detect one or more characteristics of the cardiac signal sensed within one or more particular classification windows, and classify a cardiac response to the pacing pulse based on the one or more characteristics and the particular classification windows.

69. The device of claim 68, wherein the sensing circuit is configured to sense the cardiac signal through a sensing electrode combination that is less sensitive to a pacing artifact relative to a pacing electrode combination.

70. The device of claim 68, wherein the sensing circuit is configured to sense the cardiac signal through an electrode combination associated with a signal propagation delay relative to a pacing pulse delivery time.

71. The device of claim 68, wherein:
the pacing pulse delivery circuit is configured to deliver pacing stimulations using electrodes associated with a near-field vector; and
the sensing circuit is configured to sense the cardiac signals using a far-field vector.

72. The device of claim 68, wherein the control circuit is further comprised to detect noise on the cardiac signal and cancel classification of the cardiac response to pacing based on the detection of noise.

73. The device of claim 68, wherein the control circuit is configured to define a first classification window based on a timing of a cardiac signal feature associated with a captured response and to define one or more additional classification windows relative to the first classification window.

74. The device of claim 68, wherein the control circuit is configured to compare the one or more characteristics to one or more references respectively associated with one or more types of cardiac responses.

75. The device of claim 74, wherein the control circuit is configured to adapt the one or more references.

76. The device of claim 68, wherein the control circuit is configured to classify the cardiac response to the pacing pulse as a captured response.

77. The device of claim 68, wherein the control circuit is configured to classify the cardiac response to the pacing pulse as a non-captured response.

78. The device of claim 68, wherein the control circuit is configured to classify the cardiac response to the pacing pulse as a near non-captured response.

79. The device of claim 68, wherein the control circuit is configured to classify the cardiac response to the pacing pulse as a non-captured response and an intrinsic beat.

80. The device of claim 68, wherein the control circuit is configured to classify the cardiac response to the pacing pulse as a fusion/pseudofusion beat.

81. The device of claim 68, wherein the control circuit is configured to classify the cardiac response to the pacing pulse on a beat by beat basis.

82. The device of claim 68, wherein the control circuit is configured to use the classification of the cardiac pacing response to determine a pacing energy capture threshold.

83. The device of claim 68, wherein the controller is configured to modify at least one of the first, second, and third classification windows.

84. A medical device for classifying a cardiac pacing response, comprising:
means for defining a plurality of classification windows relative to and subsequent to the pacing pulse, wherein the plurality of windows comprise a first classification window predominantly associated with a captured response, a second classification window predominantly associated with a fusion/pseudofusion response, and a third classification window predominantly associated with a non-captured response;
means for sensing a cardiac signal following the pacing pulse;
means for detecting one or more characteristics of the cardiac signal within one or more particular classification windows of the plurality of classification windows; and
means for classifying the cardiac response to the pacing pulse based on the one or more characteristics and the one or more particular classification windows.

85. The device of claim 84, further comprising:
means for detecting noise on the cardiac signal; and
means for canceling classification of the cardiac response based on the detection of noise.

86. A medical device for classifying cardiac responses to pacing, comprising:
means for delivering a sequence of pacing stimulations to a heart;
means for defining a plurality of classification windows relative and subsequent to each pacing stimulation, wherein the plurality of windows comprise;
means for sensing cardiac signals following the pacing stimulations
means for detecting characteristics of the cardiac signals within particular classification windows,
means for comparing one or more of the characteristics of the cardiac signals to a captured response template and an intrinsic response template; and
means for classifying a cardiac pacing response as a fusion/pseudofusion beat if the one or more characteristics are not consistent with the captured response template or the intrinsic response template.

87. The device of claim 86, further comprising means for using the classifications of the cardiac pacing responses to determine a pacing energy capture threshold.

88. A medical device for cardiac response verification, comprising:
means for delivering a pacing stimulation;
means for defining a plurality of classification windows relative and subsequent to the pacing stimulation, wherein the plurality of windows comprise a first classification window predominantly associated with a captured response, a second classification window predominantly associated with a fusion/pseudofusion response, and a third classification window predominantly associated with a non-captured response;
means for sensing a cardiac signal following the pacing stimulation;
means for detecting a peak of the sensed cardiac signal occurring within a particular classification window; and
means for determining a cardiac response based on the detected peak and the particular classification window.

* * * * *

UNITED STATES PATENT AND TRADEMARK OFFICE
CERTIFICATE OF CORRECTION

PATENT NO. : 7,319,900 B2 Page 1 of 1
APPLICATION NO. : 10/733869
DATED : January 15, 2008
INVENTOR(S) : Kim et al.

It is certified that error appears in the above-identified patent and that said Letters Patent is hereby corrected as shown below:

Col. 14, line 24: "be Used to" should read --be used to--.

Col. 28, line 3: "for a positive Feature" should read --for a positive Feature 3--.

Col. 28, line 5: "$Q(I-1) \geqq Q(I)$ and" should read --$Q(I-1) \leq Q(I)$ and--.

Col. 34 lines 8-9

Claim 47, "fusion/Pseudofusion response." should read --fusion/pseudofusion response.--.

Signed and Sealed this

Seventeenth Day of June, 2008

JON W. DUDAS
*Director of the United States Patent and Trademark Office*